US012582702B2

(12) United States Patent
Wang et al.

(10) Patent No.: US 12,582,702 B2
(45) Date of Patent: Mar. 24, 2026

(54) METHODS FOR IMPROVING LEPTIN SENSITIVITY FOR THE TREATMENT OF OBESITY AND DIABETES

(71) Applicant: University of Massachusetts, Boston, MA (US)

(72) Inventors: Yong-Xu Wang, Southborough, MA (US); Lei Huang, Shrewsbury, MA (US); Yong Du, Houston, TX (US)

(73) Assignee: University of Massachusetts, Westborough, MA (US)

( * ) Notice: Subject to any disclaimer, the term of this patent is extended or adjusted under 35 U.S.C. 154(b) by 1155 days.

(21) Appl. No.: 17/054,334

(22) PCT Filed: May 9, 2019

(86) PCT No.: PCT/US2019/031558
§ 371 (c)(1),
(2) Date: Nov. 10, 2020

(87) PCT Pub. No.: WO2019/217706
PCT Pub. Date: Nov. 14, 2019

(65) Prior Publication Data
US 2021/0162011 A1      Jun. 3, 2021

Related U.S. Application Data

(60) Provisional application No. 62/670,568, filed on May 11, 2018.

(51) Int. Cl.

| | |
|---|---|
| *C07H 21/04* | (2006.01) |
| *A61K 9/00* | (2006.01) |
| *A61K 38/22* | (2006.01) |
| *A61K 38/24* | (2006.01) |
| *A61K 38/38* | (2006.01) |
| *A61K 38/40* | (2006.01) |
| *A61P 3/04* | (2006.01) |
| *A61P 3/10* | (2006.01) |
| *C07K 14/575* | (2006.01) |
| *C07K 14/59* | (2006.01) |
| *C07K 14/765* | (2006.01) |
| *C07K 14/79* | (2006.01) |
| *C07K 16/26* | (2006.01) |
| *C12N 7/00* | (2006.01) |
| *C12N 15/113* | (2010.01) |
| *C12N 15/86* | (2006.01) |

(52) U.S. Cl.
CPC ........ *A61K 38/2264* (2013.01); *A61K 9/0019* (2013.01); *A61K 9/0029* (2013.01); *A61K 38/24* (2013.01); *A61K 38/385* (2013.01); *A61K 38/40* (2013.01); *A61P 3/04* (2018.01); *A61P 3/10* (2018.01); *C07K 14/5759* (2013.01); *C07K 14/59* (2013.01); *C07K 14/765* (2013.01); *C07K 14/79* (2013.01); *C07K 16/26* (2013.01); *C12N 7/00* (2013.01); *C12N 15/1136* (2013.01); *C12N 15/86* (2013.01); *C07K 2319/00* (2013.01); *C12N 2310/11* (2013.01); *C12N 2310/122* (2013.01); *C12N 2310/14* (2013.01); *C12N 2310/31* (2013.01); *C12N 2310/3231* (2013.01); *C12N 2310/33* (2013.01); *C12N 2310/341* (2013.01); *C12N 2310/531* (2013.01); *C12N 2320/32* (2013.01); *C12N 2750/14143* (2013.01)

(58) Field of Classification Search
None
See application file for complete search history.

(56) References Cited

U.S. PATENT DOCUMENTS

2007/0053910 A1      3/2007 Frigerio et al.

FOREIGN PATENT DOCUMENTS

| WO | WO/2004/031411 | * | 4/2004 |
|---|---|---|---|
| WO | WO2007013358 | * | 2/2007 |
| WO | WO 2017/042318 | | 3/2017 |

OTHER PUBLICATIONS

Aguilera et al., "Genome-wide expression in visceral adipose tissue from obese prepubertal children," International Journal of Molecular Sciences, Apr. 2015, 16(4):7723-37.

Bauwens et al., "Cold tolerance, cold-induced byperphagia, and nonshivering thermogenesis are normal in αl-AMPK-/- mice," American Journal of Physiology-Regulatory, Integrative and Comparative Physiology, Aug. 2011, 301(2):R473-83.

Bendtsen et al., "Feature-based prediction of non-classical and leaderless protein secretion, " Protein Engineering Design and Selection, Apr. 1, 2004, 17(4):349-56.

Cannon et al., "Brown adipose tissue: function and physiological significance, " Physiological Reviews, Jan. 2004, 84(1):277-359.

Chen et al., "Salidroside alleviates cachexia symptoms in mouse models of cancer cachexia via activating mTOR signalling," Journal of Cachexia, Sarcopenia and Muscle, May 2016, 7(2):225-32.

Christopoulos, "Allosteric binding sites on cell-surface receptors: novel targets for drug discovery," Nature Reviews Drug discovery, Mar. 2002, 1(3):198-210.

Cohen et al., "Selective deletion of leptin receptor in neurons leads to obesity," The Journal of Clinical Investigation, Oct. 15, 2001, 108(8):1113-21.

(Continued)

*Primary Examiner* — Meera Natarajan
(74) *Attorney, Agent, or Firm* — Fish & Richardson P.C.

(57) ABSTRACT

Methods for altering leptin resistance and the hormonal control of energy balance, and methods for treating obesity and diabetes, as well as promoting weight gain, using batotin and batotin inhibitors.

16 Claims, 10 Drawing Sheets

Specification includes a Sequence Listing.

(56) References Cited

OTHER PUBLICATIONS

Coll et al., "The hormonal control of food intake," Cell, Apr. 20, 2007, 129(2):251-62.

Coppari et al., "Leptin revisited: its mechanism of action and potential for treating diabetes," Nature Reviews Drug discovery, Sep. 2012, 11(9):692-708.

Coppari et al., "The hypothalamic arcuate nucleus: a key site for mediating leptin's effects on glucose homeostasis and locomotor activity," Cell Metabolism, Jan. 1, 2005, 1(1):63-72.

Cui et al., "The cellular and molecular bases of leptin and ghrelin resistance in obesity," Nature Reviews Endocrinology, Jun. 2017, 13(6):338-51.

Cummings et al., "Subcutaneous administration of leptin normalizes fasting plasma glucose in obese type 2 diabetic UCD-T2DM rats.," Proceedings of the National Academy of Sciences, Aug. 30, 2011, 108(35):14670-5.

Dalamaga et al., "Leptin at the intersection of neuroendocrinology and metabolism: current evidence and therapeutic perspectives," Cell Metabolism, Jul. 2, 2013, 18(1):29-42.

Duerrschmid et al., "Asprosin is a centrally acting orexigenic hormone," Nature Medicine, Dec. 2017, 23(12):1444-53.

Eguchi et al., "Transcriptional control of adipose lipid handling by IRF4," Cell Metabolism, Mar. 2, 2011. 13(3):249-59.

Flak et al., "Minireview: CNS mechanisms of leptin action," Molecular Endocrinology, Jan. 1, 2016, 30(1):3-12.

Fujikawa et al., "Leptin therapy improves insulin-deficient type 1 diabetes by CNS-dependent mechanisms in mice," Proceedings of the National Academy of Sciences, Oct. 5, 2010, 107(40):17391-6.

Fukuda et al., "Induction of leptin resistance by activation of cAMP-Epac signaling," Cell Metabolism, Mar. 2, 2011, 13(3):331-9.

Ge et al., "LEAP2 is an endogenous antagonist of the ghrelin receptor," Cell Metabolism, Feb. 6, 2018. 27(2):461-9.

GenBank Accession No. Q96GX8, Uncharacterized protein C16orf74, Dec. 12, 2006 retrieved Jan. 19, 2021 from the internet from URL <https://www.ncbi.nlm.nih.gov/protein/74731865?sat=34&satkey= 11658728>, 2 pages.

Harms et al., "Brown and beige fat: development, function and therapeutic potential," Nature Medicine, Oct. 2013, 19(10):1252-63.

Huang et al., "Transcription factor Hlx controls a systematic switch from white to brown fat through Prdm16-mediated co-activation," Nature Communications, Jul. 12, 2017, 8(1):1-6.

Huo et al., "Leptin-dependent control of glucose balance and locomotor activity by POMC neurons," Cell Metabolism, Jun. 3, 2009, 9(6):537-47.

Iserentant et al., "Mapping of the interface between leptin and the leptin receptor CRH2 domain," Journal of Cell Science, Jun. 1, 2005, 118(11):2519-27.

Kajimura et al., "Brown and beige fat: physiological roles beyond heat generation," Cell Metabolism, Oct. 6, 2015, 22(4):546-59.

Kusminski et al., "MitoNEET-mediated effects on browning of white adipose tissue," Nature Communications, May 28, 2014, 5(1):1-4.

Lee et al., "Withaferin A is a leptin sensitizer with strong antidiabetic properties in mice," Nature Medicine, Sep. 2016, 22(9):1023-32.

Leininger et al., "Leptin acts via leptin receptor-expressing lateral hypothalamic neurons to modulate the mesolimbic dopamine system and suppress feeding," Cell Metabolism, Aug. 6, 2009. 10(2):89-98.

Loh et al., "Elevated hypothalamic TCPTP in obesity contributes to cellular leptin resistance," Cell Metabolism, Nov. 2, 2011, 14(5):684-99.

Long et al., "The secreted enzyme PM20D1 regulates lipidated amino acid uncouplers of mitochondria," Cell, Jul. 14, 2016, 166(2):424-35.

Lowell et al., "Towards a molecular understanding of adaptive thermogenesis," Nature, Apr. 2000, 404(6778):652-60.

Misu et al., "A liver-derived secretory protein, selenoprotein P, causes insulin resistance," Cell Metabolism, Nov. 3, 2010, 12(5):483-95.

Morton et al., "Neurobiology of food intake in health and disease," Nature Reviews Neuroscience, Jun. 2014, 15(6):367-78.

Mosialou et al., "MC4R-dependent suppression of appetite by bone-derived lipocalin 2," Nature, Mar. 2017, 543(7645):385-90.

Mueller et al., "Production and Discovery of Novel Recombinant Adeno-Associated Viral Vectors," Current Protocols in Microbiology, Aug. 2012, 26(1):14D, 21 pages.

Myers Jr et al., "The geometry of leptin action in the brain: more complicated than a simple ARC," Cell Metabolism, Feb. 4, 2009. 9(2):117-23.

Nakai et al., "Up-regulation of genes related to the ubiquitin-proteasome system in the brown adipose tissue of 24-h-fasted rats," Bioscience, Biotechnology, and Biochemistry, Jan. 23, 2008, 72(1):139-48.

Nakamura et al., "Overexpression of C16orf74 is involved in aggressive pancreatic cancers," Oncotarget, Aug. 1, 2017, 8(31):50460, 16 pages.

Oral et al., "Leptin-replacement therapy for lipodystrophy," New England Journal of Medicine, Feb. 21, 2002, 346(8):570-8.

Ozcan et al., "Endoplasmic reticulum stress plays a central role in development of leptin resistance," Cell metabolism, Jan. 7, 2009, 9(1):35-51.

Pan et al., "Jmjd3-mediated H3K27me3 dynamics orchestrate brown fat development and regulate white fat plasticity," Developmental Cell, Dec. 7, 2015, 35(5):568-83.

Pan et al., "Twist-1 is a PPARδ-inducible, negative-feedback regulator of PGC-1α in brown fat metabolism," Cell, Apr. 3, 2009, 137(1):73-86.

PCT International Preliminary Report on Patentability in International Appln. No. PCT/US2019/031558, dated Nov. 17, 2020, 10 pages.

PCT International Search Report and Written Opinion in International Appln. No. PCT/US2019/031558, dated Sep. 23, 2019, 14 pages.

Peelman et al., "20 years of leptin: insights into signaling assemblies of the leptin receptor," Journal of Endocrinology, Oct. 1, 2014, 223(1):T9-23.

Petersen et al., "Leptin reverses insulin resistance and hepatic steatosis in patients with severe lipodystrophy," The Journal of Clinical Investigation, May 15, 2002, 109(10):1345-50.

Postic et al., "Dual roles for glucokinase in glucose homeostasis as determined by liver and pancreatic β cell-specific gene knock-outs using Cre recombinase," Journal of Biological Chemistry, Jan. 1, 1999. 274(1):305-15.

Pritchard et al., "Agouti-related protein (83-132) is a competitive antagonist at the human melanocortin-4 receptor: no evidence for differential interactions with pro-opiomelanocortin-derived ligands," Journal of Endocrinology, Jan. 1, 2004, 180(1):183-92.

Rajbhandari et al., "IL-10 signaling remodels adipose chromatin architecture to limit thermogenesis and energy expenditure," Cell, Jan. 11, 2018, 172(1-2):218-33.

Ravussin et al., "Effect of intermittent cold exposure on brown fat activation, obesity, and energy homeostasis in mice," PloS One, Jan. 17, 2014, 9(1):e85876, 9 pages.

Ren et al., "Identification of SH2-B as a key regulator of leptin sensitivity, energy balance, and body weight in mice," Cell Metabolism, Aug. 1, 2005, 2(2):95-104.

Rosen et al., "What we talk about when we talk about fat," Cell, Jan. 16, 2014, 156(1-2):20-44.

Rousso-Noori et al., "Protein tyrosine phosphatase epsilon affects body weight by downregulating leptin signaling in a phosphorylation-dependent manner," Cell Metabolism, May 4, 2011, 13(5):562-72.

Sato et al., "Molecular targeting of cell-permeable peptide inhibits pancreatic ductal adenocarcinoma cell proliferation," Oncotarget, Dec. 26, 2017, 8(69):113662-72.

Scott et al., "Leptin targets in the mouse brain. Journal of Comparative Neurology," Jun. 10, 2009, 514(5):518-32.

(56) References Cited

OTHER PUBLICATIONS

Shimomura et al., "Leptin reverses insulin resistance and diabetes mellitus in mice with congenital lipodystrophy," Nature, Sep. 1999, 401(6748):73-6.

Stanford et al., "A novel role for subcutaneous adipose tissue in exercise-induced improvements in glucose homeostasis." Diabetes, Jun. 1, 2015, 64(6):2002-14.

Stanley et al., "Hormonal regulation of food intake," Physiological Reviews, Oct. 1, 2005, 85:1131-58.

Tartaglia et al, "Identification and expression cloning of a leptin receptor, OB-R," Cell, Dec. 29. 1995. 83(7):1263-71.

Wang et al., "The brown fat-enriched secreted factor Nrg4 preserves metabolic homeostasis through attenuation of hepatic lipogenesis," Nature Medicine, Dec. 2014, 20(12):1436, 22 pages.

Wauman et al., "The leptin receptor complex: heavier than expected?," Frontiers in Endocrinology, Feb. 21, 2017, 8:30.

Williams et al., "From neuroanatomy to behavior: central integration of peripheral signals regulating feeding behavior," Nature Neuroscience, Oct. 2012, 15(10):1350-5.

Yu et al., "Making insulin-deficient type 1 diabetic rodents thrive without insulin," Proceedings of the National academy of Sciences, Sep. 16, 2008, 105(37):14070-5.

Zhang et al., "Positional cloning of the mouse obese gene and its human homologue, " Nature, Dec. 1, 1994, 372(6505):425-32.

EP European Search Report in European Appln. No. 19800879.9, dated Feb. 11, 2022, 9 pages.

EP Office Action in European Appln. No. 19800879.9, mailed on Feb. 14, 2024, 6 pages.

* cited by examiner

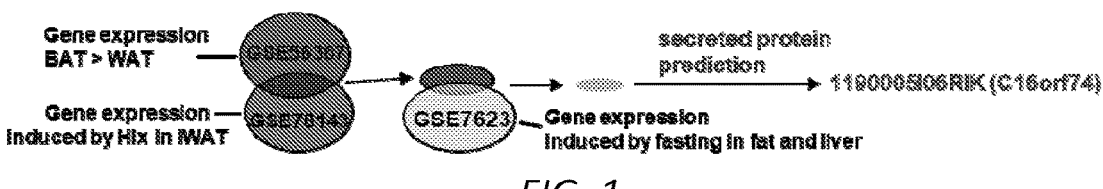
*FIG. 1*
mouse MTPAAHGCKRVAWCPSRPPASAPSAPQEAARRGDAMGLKPSCLKGFKMCVSSSNNNHDEAPVLNDKHLSVPNIII
                                 MGLK SCLKGF+MCVSSS+++HDEAPVLNDKHL VP+III
human                          1 MGLKMSCLKGFQMCVSSSSSSHDEAPVLNDKHLDVPDIII
mouse TPPTPTGMGLSRDSNKQVWMDELGSYQDDGELEPEA
      TPPTPTGM L RD    VW+DE GS   DDGE++PEA
human TPPTPTGMMLPRDLGSTVWLDETGSCPDDGEIDPEA 76
*FIG. 2*
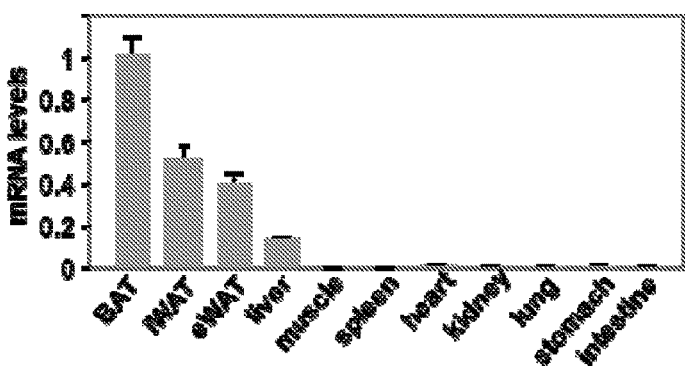
*FIG. 3A*
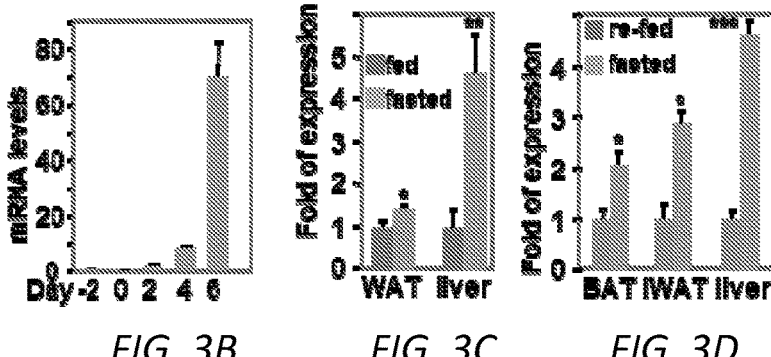
*FIG. 3B*          *FIG. 3C*          *FIG. 3D*

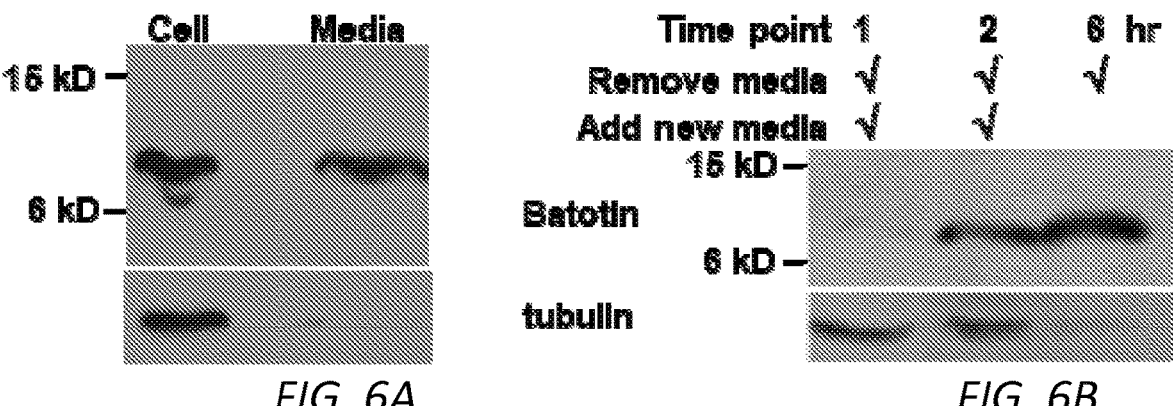
FIG. 6A
FIG. 6B
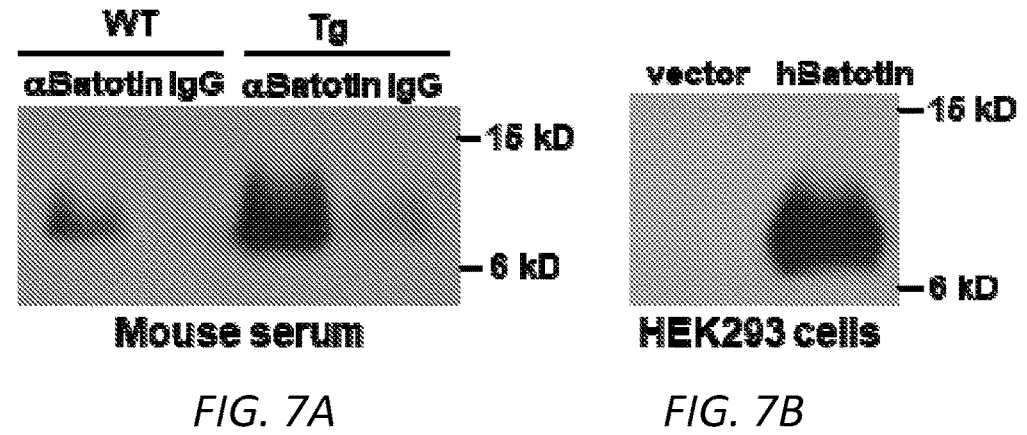
FIG. 7A
FIG. 7B
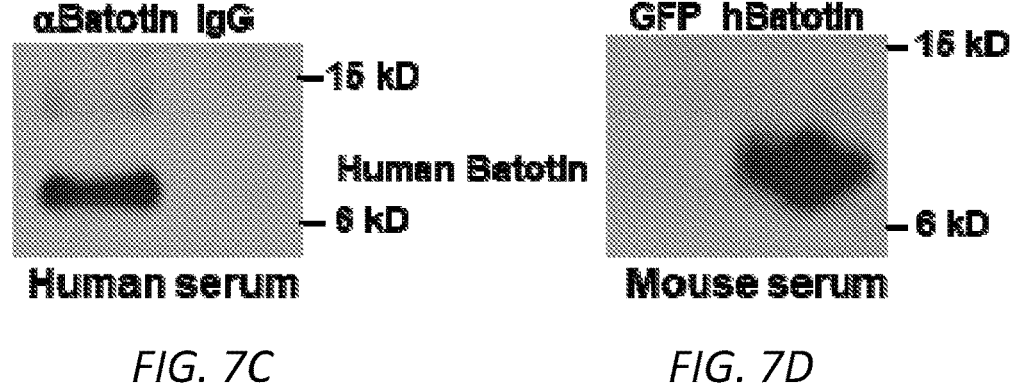
FIG. 7C
FIG. 7D

Fig. 16. Genotyping of Batotin conditional KO mice (F1).

METHODS FOR IMPROVING LEPTIN SENSITIVITY FOR THE TREATMENT OF OBESITY AND DIABETES

CLAIM OF PRIORITY

This application is a National Stage Application under 35 U.S.C. § 371 and claims the benefit of International Application No. PCT/US2019/031558, filed May 9, 2019, which claims priority under 35 USC § 119 (e) to U.S. Patent Application Ser. No. 62/670,568, filed on May 11, 2018. The entire contents of each of the foregoing are hereby incorporated by reference.

FEDERALLY SPONSORED RESEARCH OR DEVELOPMENT

This invention was made with Government support under Grant Nos. DK076118 and DK098594 awarded by the National Institutes of Health. The Government has certain rights in the invention.

SEQUENCE LISTING

This application contains a Sequence Listing that has been submitted electronically as ASCII text file named 07917-0408US1_ST25.txt. The ASCII text file, created on Feb. 3, 2025, is 6,691 bytes in size. The material in the ASCII text file is hereby incorporated by reference in its entirety.

TECHNICAL FIELD

Described herein are methods for altering leptin resistance and the hormonal control of energy balance, and methods for treating obesity and diabetes, as well as promoting weight gain, using batotin and batotin inhibitors.

BACKGROUND

Energy homeostasis is largely controlled by communications between peripheral tissues and the central nervous system (CNS). In response to changes of the body's energy reserves and nutritional status, peptides are secreted from peripheral tissues to regulate signaling pathways in hypothalamus and brainstem, which in turn modulate food intake. Indeed, a number of anorexigenic peptides have been identified. These include leptin [produced by white fat (WAT)], insulin (produced by pancreatic b cells), lipocalin 2 (LCN2) (produced by bone and WAT), Cholecystokinin (CCK) (produced by duodenum), Glucagon-like peptide 1 (GLP-1) (produced by gut-endocrine L cells), PYY3-36 (produced by L cells), and LEAP2 (produced by small intestine and liver)[15]. In contrast, appetite-stimulating pathways elicited by peripheral tissues were less understood. Two secreted peptides, Ghrelin and Asprosin, produced by stomach and adipose tissues, respectively, were shown to have orexigenic effects[6, 7]

The leptin signaling pathway is considered the most critical anorexigenic pathway in the control of food intake[6, 8-12]. Leptin and its receptor were identified more than 30 years ago[13, 14]. Leptin is a 16 kD adipokine that is almost exclusively produced by WAT. Leptin receptor is primary expressed in the hypothalamus. Although several splice variants of leptin receptor exist, the longest form (LepRb) mediates all actions of leptin. Circulating leptin levels are directly proportional to the amount of body fat, and are increased during overfeeding and decreased during fasting.

In the hypothalamus, upon binding of leptin, the LepRb receptor dimerizes and undergoes a conformational change; this leads to the activation of multiple kinase pathways[6, 8-11]. Among them is the JAK2/STAT3 pathway. Activated JAK2 phosphorylates STAT3, which in turn translocates into nucleus to regulate expression of target genes that are important for food intake. In addition, leptin has been shown to improve hyperglycemia in animal models of type 1 and type 2 diabetes and humans with lipodystrophys[15-22]. Importantly, its anti-diabetic function is independent of its regulation of body weight and food intake. Studies suggest that the effects of leptin and leptin receptor on food intake, glucose homeostasis, and other physiological processes are mediated by specific neurons in the hypothalamus[4, 6, 8, 10, 11]

SUMMARY

The present invention is based, at least in part, on the discovery that Batotin, acting as an orexigenic hormone, binds to leptin receptor to suppress leptin signaling and promotes food intake and body weight gain. Thus, provided herein are methods for altering leptin resistance and the hormonal control of energy balance, and methods for treating obesity and diabetes, as well as promoting weight gain, using batotin and batotin inhibitors.

Thus, provided herein are methods for treating, or reducing risk of, a disorder associated with underweight or weight loss in a mammalian subject. The methods include comprising administering a therapeutically effective amount of batotin to a subject in need thereof.

In some embodiments, the disorder associated with underweight or weight loss is cachexia or loss of appetite, e.g., associated with chemotherapy, cancer, or chronic illness, e.g., HIV.

In some embodiments, the methods include administering (i) a polypeptide comprising a sequence that is at least 80% identical to SEQ ID NO:2, or an active fragment thereof, or (ii) a nucleic acid encoding a polypeptide comprising a sequence that is at least 80% identical to SEQ ID NO:2, or an active fragment thereof.

In some embodiments, the methods include administering (i) a polypeptide comprising a sequence that is at least 95% identical to SEQ ID NO:2, or an active fragment thereof, or (ii) a nucleic acid encoding a polypeptide comprising a sequence that is at least 95% identical to SEQ ID NO:2, or an active fragment thereof.

In some embodiments, the subject has a BMI of 18.5 or below.

In some embodiments, the subject is human.

In some embodiments, the nucleic acid is administered in a viral vector, e.g., an adeno-associated viral (AAV) vector, e.g., an AAV selected from the group consisting of AAV8, AAV-2/8, AAV2 (Y→F), AAV7, AAV-HSC15, AAV-HSC17, AAV-HSC15/17, AAVhu.37 and AAVrh.8.

In some embodiments, the polypeptide is administered parenterally. In some embodiments, the polypeptide is administered intravenously, intramuscularly, or subcutaneously.

In some embodiments, the polypeptide comprises one or more modifications, e.g., one or more of: replacement of one or more L amino acids with D amino acids; acetylation (e.g., comprises an N-acetylalanine at position 2), amidation; conjugation to a linear or branched-chain monomethoxy poly-ethylene glycol (PEG, i.e., is PEGylation); modification of the N- or C-terminus; glycosylation; polysialic acid (PSA) addition to a glycan; or fusion to a non-batotin protein, e.g., Fc fusion proteins, fusion to human serum albumin, fusion to transferrin, or fusion to carboxy-terminal peptide of chorionic gonadotropin (CG) β-chain.

Also provided herein are viral vectors comprising a nucleic acid encoding a polypeptide comprising a sequence that is at least 80% identical to SEQ ID NO:2, or an active fragment thereof. In some embodiments, the viral vector is an adeno-associated viral (AAV) vector, e.g., selected from the group consisting of AAV8, AAV-2/8, AAV2 (Y→F), AAV7, AAV-HSC15, AAV-HSC17, AAV-HSC15/17, AAVhu.37 and AAVrh.8.

In some embodiments, the viral vector includes a promoter for expression of the polypeptide in liver or adipose cells.

In addition, provided herein are isolated polypeptides that are at least 80% identical to SEQ ID NO:2, or an active fragment thereof, and comprise one or more modifications, e.g., one or more of: replacement of one or more L amino acids with D amino acids; acetylation (e.g., comprises an N-acetylalanine at position 2), amidation; conjugation to a linear or branched-chain monomethoxy poly-ethylene gly-col (PEG); modification of the N- or C-terminus; glycosylation; polysialic acid (PSA) addition to a glycan; or fusion to a non-batotin protein, e.g., Fc fusion proteins, fusion to human serum albumin, fusion to transferrin, or fusion to carboxy-terminal peptide of chorionic gonadotropin (CG) β-chain.

Further, provided herein are pharmaceutical compositions including a batotin polypeptide as described herein, or a nucleic acid encoding a batotin polypeptide as described herein, and a pharmaceutically acceptable carrier, as well as pharmaceutical compositions including a viral vector as described herein and/or an isolated polypeptide as described herein, and a pharmaceutically acceptable carrier.

These pharmaceutical compositions can be for use, e.g., in a method of treating, or reducing risk of, underweight or a disorder associated with underweight or weight loss in a mammalian subject, e.g., cachexia, weight loss, or loss of appetite.

Also provided herein are methods for treating, or reducing risk of, a disorder associated with obesity or a disorder associated with obesity, or improving glycemic control, in a mammalian subject. The methods include administering a therapeutically effective amount of a batotin inhibitory antibody or inhibitory nucleic acid to a subject in need thereof.

In some embodiments, the disorder associated with obesity is diabetes, metabolic syndrome, fatty liver disease, non-hepatic steatosis.

In some embodiments, the batotin inhibitor is an inhibitory nucleic acid, e.g., an antisense oligonucleotide, short interfering RNA (siRNA); or a short, hairpin RNA (shRNA).

In some embodiments, the subject has a BMI of at least 25, or at least 30.

In some embodiments, the subject is human.

In some embodiments, the inhibitory nucleic acid or antibody is administered parenterally. In some embodiments, the inhibitory nucleic acid or antibody is administered intravenously, intramuscularly, or subcutaneously.

In some embodiments, the inhibitory nucleic acid comprises one or more modifications, e.g., one or more modified bases or backbone.

In some embodiments, the inhibitory nucleic acid is a gapmer, mixmer, or locked nucleic acid (LNA).

Also provided herein are pharmaceutical compositions that include a batotin inhibitory antibody, or an inhibitory nucleic acid, and a pharmaceutically acceptable carrier. These pharmaceutical compositions can be used, e.g., in a method of treating, or reducing risk of, obesity or a disorder associated with obesity in a mammalian subject, e.g., diabetes, metabolic syndrome, fatty liver disease, non-hepatic steatosis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

Quantitative data presented in all figures represent mean SEM, and n represents biological samples. *$p<0.05$, $p<0.01$, *$p<0.001$.

FIG. 1. Bioinformatic analysis led to the identification of Batotin.

FIG. 2. Deduced amino acid sequences from mouse (SEQ ID NO:1) and human (SEQ ID NO:2) Batotin mRNA, with a consensus sequence in between. Mouse Batotin protein is in fact translated from an internal ATG (Methionine residue labeled in Blue), therefore both mouse and human Batotin protein has 76 amino acid residues (8 kD).

FIGS. 3A-3E. (A) RT-qPCR analysis of Batotin expression in mouse tissues (n=4 mice). (B) Batotin expression during brown adipocyte differentiation. (C) Data of Batotin expression at fed and 24-hour fasted states, downloaded from GSE7623. n=4 rats/group. (D) Batotin expression at 16-hr fasted and 2-hr re-fed states. n=3 mice/group. (E) Batotin level in iWAT after 6 hr cold exposure. N=4 mice/group. Note, data in (C) and (D) are fold of expression normalized to fed or re-fed conditions.

FIGS. 6A-6B. (A) Batotin is secreted from cultured brown adipocytes. (B) BAT tissue slice was incubated with conditioned media and presence of Batotin in media was examined at different time points.

FIGS. 7A-7D. Mouse and human Batotin proteins are present in circulation. (A) Serum from wild type mice (WT) and aP2-driven Batotin transgenic mice (Tg) was immunoprecipitated with antibodies against mouse Batotin, followed by western blot analysis. (B) Validation of antibodies against human Batotin in HEK293 cells transfected with human Batotin cDNA plasmids. (C) Human serum was immunoprecipitated with antibodies against human Batotin, followed by western blot analysis. In (A) and (C), IgG was used as a control. (D) Human Batotin was expressed in mouse liver through tail-vein adenoviral infusion; human Batotin can be detected in mouse circulation without the need of immunoprecipitation.

DETAILED DESCRIPTION

Figure 3E:
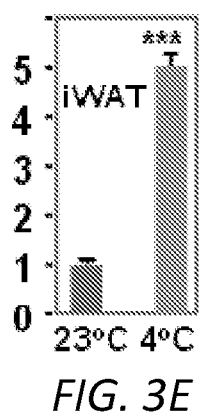

While leptin treatment recuses obesity in patients who have congenital leptin deficiency, it is ineffective in decreasing food intake, suppressing body weight gain, or improving glycaemic control in subjects with diet-induced obesity. These individuals have elevated circulating leptin levels, response poorly to exogenous leptin, and are thus considered to be leptin resistant. Therefore, elucidating the underlying mechanisms of leptin resistance is an active area of research. Much of the effort has been focused on identifying negative regulators within the hypothalamus, and a number of intracellular signaling molecules or pathways have been found to interfere with JAK2 and STAT3 phosphorylation[6, 8-10, 23, 24]. To date, whether peripheral tissues produce endocrine factors to directly antagonize leptin signaling remains to be explored.

WAT and brown fat (BAT) are two types of functionally distinct adipose tissues. WAT stores energy as triglycerides and releases them in response to energy needs, whereas BAT and brown-like (beige) adipocytes are specialized in energy expenditure through nonshivering thermogenesis[25-29]. Moreover, WAT is a well-recognized endocrine organ, and secretes a number of bioactive proteins. In contrast, the secretory role of BAT and beige adipocytes has been poorly understood, and proteins selectively secreted from these adipocytes have not been extensively identified, let alone functionally characterized. Nevertheless, recent work by others has identified two BAT-enriched adipokines, Pm20d1 and Neuregulin 4 (Nrg4), that regulate adipose mitochondrial respiration and hepatic lipogenesis, respectively[30, 31]. These studies suggest that the secretome of BAT and beige adipocytes has the potential to regulate energy metabolism both locally and systematically.

Batotin

Given the WAT-specific expression of leptin, we explored the possibility that BAT secretes an adipokine to antagonize leptin signaling. We identified a previously uncharacterized gene (1190005I06RIK in mouse, and its human ortholog C16orf74, see FIG. 1) encoding an 8 kD adipokine that is selectively expressed in the adipose tissue and liver and is highly enriched in BAT. This adipokine is referred to herein as batotin. Based on the results both in vitro and in vivo, and without wishing to be bound by theory, it is hypothesized that secreted Batotin acts as an orexigenic peptide by suppressing leptin signaling to promote food intake.

Exemplary human Batotin sequences are available in GenBank at Acc. No. NM_206967.2 (nucleic acid) and NP_996850.1 (protein), e.g., as follows:

```
Protein:
                                              (SEQ ID NO: 2)
   1 mglkmsclkg fqmcvsssss shdeapvind khldvpdiii tpptptgmml prdlgstvwl 61 detgscpddg eidpea Nucleic acid:
                                              (SEQ ID NO: 8)
   1 cccgagcgcc ggccgggcca tgaccccgc tgctctgtct tgcaggctcg tcgccgcggc 61 cccccgagcc cgaccgccgc cgccaccacc accagcgccc gggcgggcct cgcgcgcctc 121 gggcgcggct ccgcagtgag cccaccaaga aggaagcggc ctgcagaggt gccgacatgg 181 ggcttaagat gtcctgcctg aaaggctttc aaatgtgtgt cagcagcagc agcagcagcc 241 acgacgaggc ccccgtcctg aacgacaagc acctggacgt gcccgacatc atcatcacgc 301 cccccacccc cacgggcatg atgctgccga gggacttggg gagcacagtc tggctggatg 361 agacagggtc gtgcccagat gatggagaaa tcgacccaga agcctgagga ggtgtcctgg 421 gtttggctgg ctggctcctg ctccagcggc ccggcttcag gtgtccgggg gcgtggctgc 481 ctggagcagg tgtgctgaat accctggatg ggaactgagc gaacccgggc ctccgctcag 541 agagacgtgg caggaccagc gaggaatcca gcctgtccac ttccagaaca gtgtttccca 601 ggccccgctg agtggaccgg acctctgaca cctccaggtt cttgctgact ccggcctggt 661 gaaagggagc gccatggtcc tggctgttgg ggtcccaggg agaggctctc ttctggacaa 721 acacaccctc ccagccccca gggctgtgca aacacatgcc cctgccataa gcaccaacaa 781 gaacttcttg caggtggagt ggctgttttt tataagttgt tttacagata cggaaacagt 841 ccaaaatggg atttataatt tcttttttgc attataaata aagatcctct gtaacaaaa
```

Additional homologs of Batotin sequences are available in GenBank), e.g., as follows:

| Gene Symbol, Species, Gene Name | GenBank Acc. No |
|---|---|
| C16orf74, *H. sapiens* chromosome 16 open reading frame 74 | NP_996850.1 |
| C16H16orf74, *P. troglodytes* chromosome 16 open reading frame, human C16orf74 | XP_003952962.1 |

-continued

| Gene Symbol, Species, Gene Name | GenBank Acc. No |
|---|---|
| C5H16orf74, *C. lupus* chromosome 5 open reading frame, human C16orf74 | XP_005620690.1 |
| C18H16orf74, *B. taurus* chromosome 18 open reading frame, human C16orf74 | XP_002694798.1 |
| 1190005I06Rik, *M. musculus* RIKEN cDNA 1190005I06 gene | NP_932105.2 |
| RGD1309651, *R. norvegicus* similar to 1190005I06Rik protein | XP_341703.1 |

```
NP_996850.1       1 --------------------------------MGLKMSCLKGFQMCV  15

XP_003952962.1    1 --------------------------------MGLKMSCLKGFQMCV  15

XP_005620690.1    1 --------------------------------MGLKLSCLKGLKMCG  15

XP_002694798.1    1 --------------------------------MGLKLTCLKGLKMCV  15

NP_932105.2       1 MTPAAHGCKRVAWCPSRPPASAPSAPQEAARRGDAMGLKPSCLKGFKMCV  50

XP_341703.1       1 MTPAAHGCRRVAWCPSRQPASAPSAPQEAARRGDAMGLKPSCLKGFKMCV  50

NP_996850.1      16 SSSSSSHDEAPVLNDKHLDVPDIIITPPTPTGMMLPRDLGSTVWLDETGS  65

XP_003952962.1   16 SSSSSSHDEAPVLNDKHLDVPDIIITPPTPTGMMLPRDSGSTVWLDETGS  65

XP_005620690.1   16 SSSGSSHDEAPVLSDKHLDVPNIIITPPTPTGMMLPRDSRQTVWLDETGS  65

XP_002694798.1   16 SSSGS-HDEAPVLSDKHLDVPNIIITPPTPTGVALPRDTRRAVWLDESGS  64
```

-continued

| NP_932105.2 | 51 | SSSNNNHDEAPVLNDKHLSVPNIIITPPTPTGMGLSRDSNKQVWMDELGS | 100 | |
|---|---|---|---|---|
| XP_341703.1 | 51 | SSSSNNHDEAPVLNDKHLSVPNIIITPPTPTGMGLSRDSNSQVWMDELGS | 100 | |
| NP_996850.1 | 66 | CPDDGEIDPEA | 76 | SEQ ID NO: 2 |
| XP_003952962.1 | 66 | CPDDGEIDPEA | 76 | SEQ ID NO: 4 |
| XP_005620690.1 | 66 | CPEDGEIDPEA | 76 | SEQ ID NO: 5 |
| XP_002694798.1 | 65 | CTEDGDLDPEA | 75 | SEQ ID NO: 6 |
| NP_932105.2 | 101 | YQDDGELEPEA | 111 | SEQ ID NO: 1 |
| XP_341703.1 | 101 | YQDDEELEPEV | 111 | SEQ ID NO: 7 |

Figure 8A:
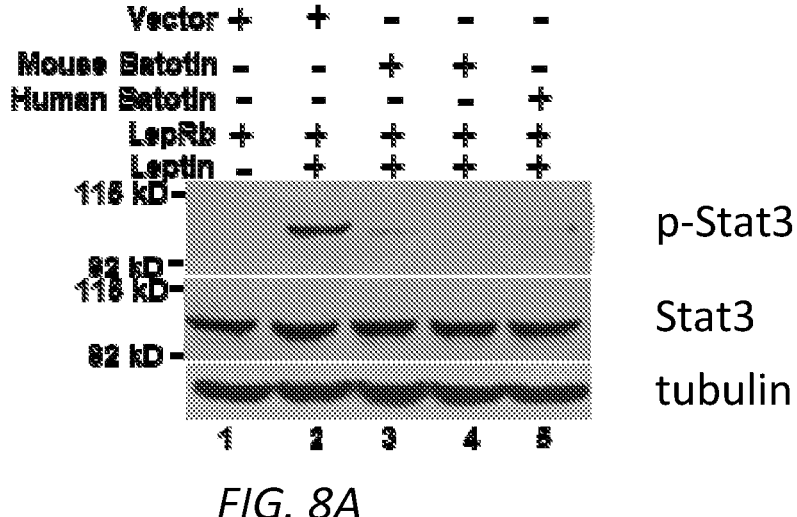
FIGS. 8A-8B. (A) Batotin suppresses leptin signaling. HEK293 cells were transfected with leptin receptor (LepRb) along with indicated plasmids and then treated with leptin (100 ng/ml) for 30 min. (B) HEK293 cells transfected with LepRb were treated with conditional media containing Batotin for 2 h followed by leptin for 30 min. Stat3 phosphorylation was examined.

The batotin compositions used in the methods described herein can include a peptide that is at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, or deleted. Alternatively, the compositions can include nucleic acids that encode peptide that is at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, or deleted. In some embodiments, mutations can be made, e.g., in amino acids that are not conserved between human and mouse, or other species (see FIG. 1 and alignment above). In some embodiments, an active fragment is used; for example, an active fragment can include amino acids 13 to 75 of SEQ ID NO:2, e.g., the Domain of unknown function (DUF4597); pfam15366. In some embodiments, the variant comprises a mutation at amino acids 44 or 46 that disrupt a phosphorylation site. In some embodiments, variants and fragments useful in the present methods retain a desired activity of the parent, e.g., the ability to stimulate food intake and body weight gain. In some embodiments, the variants and fragments inhibit leptin signaling in an in vitro assay, e.g., using cultured mammalian cells (e.g., HEK293 cells) in which leptin signaling has been reconstituted (see FIGS. 8 and 9B), e.g., to test whether Batotin fragments or variants are active and whether Batotin antibodies are inhibitory.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. See, e.g., Altschul et al. (2005) FEBS J. 272:5101-5109. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blosum62 scoring matrix with a gap penalty of 11,1.

In some embodiments, the protein includes one or more modifications, e.g., is acetylated (e.g., comprises an N-acetylalanine at position 2), amidated, conjugation to either linear or branched-chain monomethoxy poly-ethylene glycol (PEG, i.e., PEGylation), modification of the N- or C-terminus, glycosylation, polysialic acid (PSA) addition to a glycan, or fusion proteins, e.g., Fc fusion proteins, fusion to human serum albumin, fusion to carboxy-terminal peptide, and other polypeptide fusion approaches to make drugs with more desirable pharmacokinetic profiles; see, e.g., Werle and Bernkop=Schnurch, Amino Acids. 2006 June; 30(4):351-67; Strohl, BioDrugs. 2015; 29(4): 215-239.

Methods of Treatment

The methods described herein include methods for the treatment of obesity and disorders associated with obesity, e.g., diabetes and metabolic syndrome. In some embodiments, the disorder is diet-induced obesity, e.g., high-calorie or high-fat diet induced obesity. Generally, the methods include administering a therapeutically effective amount of a batotin inhibitor, e.g., an inhibitory antibody or inhibitory nucleic acid targeting batotin as described herein, to a subject who is in need of, or who has been determined to be in need of, such treatment. Also described herein are methods for the treatment of underweight or cachexia. Generally, these methods include administering a therapeutically effective amount of a batotin peptide or nucleic acid encoding the batotin peptide as described herein, to a subject who is in need of, or who has been determined to be in need of, such treatment.

As used in this context, to "treat" means to ameliorate at least one symptom of obesity or a disorder associated with obesity. Often, obesity results in hyperglycemia; thus, a treatment can result in a reduction in blood glucose levels and a return or approach to normoglycemia, and/or a reduction in BMI. Administration of a therapeutically effective amount of a compound described herein for the treatment of obesity will result in decreased body weight or fat.

Also described herein are methods for the treatment of underweight or cachexia. Generally, these methods include administering a therapeutically effective amount of a batotin peptide or nucleic acid encoding the batotin peptide as described herein, to a subject who is in need of, or who has been determined to be in need of, such treatment. In some embodiments the subjects have cachexia or weight loss associated with chronic illnesses or treatments therefor and/or loss of appetite, e.g., due to chemotherapy, age, nausea, liver or kidney disease, stress, depression, digestive problems or disorders, dyspepsia, dysphagia, thyroid disorder, hormonal imbalances and chronic illnesses (e.g., HIV or cancer). As used in this context, to "treat" means to ameliorate at least one symptom of underweight or cachexia. For example, a treatment can result in an increase in food intake and/or an increase in BMI. Administration of a therapeutically effective amount of a compound described herein for the treatment of underweight or cachexia will result in increased body weight or fat.

Diabetic and Pre-Diabetic Subjects

In some embodiments, the subjects treated by the methods described herein have diabetes, i.e., are diabetic. A person who is diabetic has one or more of a Fasting Plasma Glucose Test result of 126 mg/dL or more; a 2-Hour Plasma Glucose Result in a Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and beta-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes. Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

As shown herein, inhibitors of batotin can improve glucose homeostasis in both lean and obese mice. So inhibitors of batotin can be used to improve glycemic control in diabetic patients (regardless of whether they are obese or not). This includes improving the maintenance of blood glucose levels within a desired range, e.g., maintaining a hemoglobin A1c (HbA1c) level below a desired range, e.g., below 7%.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared ($BMI=kg/m^2$). Accepted interpretations are given in Table 3.

TABLE 3

| Category | BMI |
|---|---|
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects), and administering one or more inhibitors of batotin.

Underweight can also be associated with health problems including malnutrition, vitamin deficiencies, or anemia; osteoporosis from vitamin D and calcium deficiency; decreased immune function; infertility, e.g., associated with irregular menstrual cycles; and growth and development issues, especially in children and teenagers. In some embodiments, the methods described herein include selecting subjects who have a BMI of 18.5 or below (i.e., underweight subjects), or subjects who have cachexia or other weight loss associated with chronic illnesses or treatments therefor, or loss of appetite, and administering one or more inhibitors of batotin.

Metabolic Syndrome

In some embodiments, the methods include determining whether a subject has the metabolic syndrome, and selecting the subject if they do have the metabolic syndrome, then administering an inhibitory nucleic acid as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes. 37(12):1595-1607 (1988)), refers to a clustering of obesity, dyslipidemia, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Inhibitory Antibodies

Also provided herein are methods and compositions that use inhibitory batotin antibodies. The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody; in preferred embodiments, the antibody is not polyclonal. In some embodiments the antibody has effector function and can fix complement, or can do neither. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume* 1 (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

In some embodiments, antibodies useful in the present methods and compositions are those that are inhibitory, i.e., that binds to Batotin and neutralizes the biological activity of Batotin, e.g., on leptin signaling.

Inhibitory Nucleic Acids

Inhibitory nucleic acids useful in the present methods and compositions include antisense oligonucleotides, ribozymes, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that hybridize to at least a portion of the target batotin nucleic acid and modulate its function to reduce expression, activity, or levels of batotin. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this disclosure, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. Ina more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $\text{min}^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $\text{min}^{-1}$. In addition, it is known that certain modified hammerhead ribozymes that have substrate binding arms made of DNA catalyze RNA cleavage with multiple turn-over rates that approach 100 min-.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 Nov.; 60(9):633-8; Ørom et al., Gene. 2006 May 10; 372( ):137-41). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2-amino and 2'O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2—NH—O—CH2, CH, ~N(CH3)~O~CH2 (known as a methylene(methylimino) or MMI backbone], CH2—O—N (CH3)—CH2, CH2—N(CH3)—N(CH3)—CH2 and O—N (CH3)—CH2—CH2 backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444;

5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0—$CH_2CH_2OCH_3$, also known as 2'—O-(2-methoxyethyl)] (Martin et al, Helv. Chim. Acta, 1995, 78, 486). Other preferred modifications include 2'-methoxy (2'—O—$CH_3$), 2'-propoxy (2'—$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'—O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S- tritylthiol (Manoharan et al, Ann. N. Y. Acad. Sci., 1992, 660, 306-309; Manoharan et al., Bioorg Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), aphospholipid, e.g., di-hexadecyl-rac-glycerol or triethylammonium 1,2-di-O-hexadecyl-rac-glyc-ero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), apalmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glyc-ero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335;

4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034, 133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2-modified nucleotide, e.g., a 2'-deoxy, 2'-deoxy-2'-fluoro, 2'—O-methyl, 2'—O-methoxyethyl (2'—O-MOE), 2'—O-aminopropyl (2'—O-AP), 2'—O-dimethyl-aminoethyl (2'—O-DMAOE), 2'—O-dimethylaminopropyl (2'—O-DMAP), 2'—O-dimethylaminoethyloxyethyl (2'—O-DMAEOE), or 2'—O—N-methylacetamido (2'—O-NMA). As another example, the nucleic acid sequence can include at least one 2'—O-methyl-modified nucleotide, and in some embodiments, all of the nucleotides include a 2'—O-methyl modification. In some embodiments, the nucleic acids are "locked," i.e., comprise nucleic acid analogues in which the ribose ring is "locked" by a methylene bridge connecting the 2'—O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Gene Therapy

The nucleic acids described herein, e.g., nucleic acids encoding a batotin polypeptide or active fragment thereof, or a batotin inhibitory nucleic acid, can be incorporated into a gene construct to be used as a part of a gene therapy protocol. Provided herein are expression vectors for in vivo transfection and expression of a polynucleotide that encodes a batotin polypeptide or active fragment thereof, or a batotin inhibitory nucleic acid, as described herein, e.g., in particular cell types, especially hepatic or adipose cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include TCrip, TCre, T2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). In some embodiments, a liver-tropic AAV is used, e.g., AAV8, AAV-2/8, AAV2 (Y→F), AAV7, AAV-HSC15, AAV-HSC17, AAV-HSC15/17, AAVhu.37 and AAVrh.8. See, e.g., Hu et al., Mol Ther. 2012 February; 20(2): 267-274; Asokan et al., Molecular Therapy 20(4): 699-708 (2012).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell.

Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

The gene delivery system can include one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. In some embodiments, the viral vectors used in the methods and compositions herein include a promoter for expression of the polypeptide in liver or adipose cells. For example, for liver expression, a human thyroid hormone-binding globulin promoter (see, e.g., ll, C. R. et al. Optimization of the human factor VIII complementary DNA expression plasmid for gene therapy of hemophilia A. Blood coagulation & fibrinolysis: an international journal in haemostasis and thrombosis 8 Suppl 2, S23-30 (1997)) or albumin promoter can be used. For adipose expression, an aP2 promoter (see, e.g., Ross, S. R. et al. A fat-specific enhancer is the primary determinant of gene expression for adipocyte P2 in vivo. Proceedings of the National Academy of Sciences of the United States of America 87, 9590-9594 (1990)) or adiponectin promoter (see, e.g., Eguchi, J. et al. Transcriptional control of adipose lipid handling by IRF4. Cell metabolism 13, 249-259 (2011)) can be used.

In addition to viral transfer methods, such as those illustrated above, non-viral methods can also be employed to cause expression of a nucleic acid compound described herein (e.g., a batotin nucleic acid or batotin inhibitory nucleic acid) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21): 1867-74 (2000).

In some embodiments, a batotin inhibitory nucleic acid or a sequence encoding batotin or a batotin inhibitory nucleic acid as described herein is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include batotin peptides, inhibitory antibodies, batotin nucleic acids, or inhibitory nucleic acids described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of preferred routes of administration include parenteral, e.g., intravenous, intramuscular, or subcutaneous administration.

Methods of formulating suitable pharmaceutical compositions are known in the art, see, e.g., the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various anti-bacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the batotin peptides or inhibitors are formulated with, e.g., liposomes or micelles. Biodegradable microparticle or nanoparticle delivery systems that increase intracellular uptake, e.g., polymeric and surface modified nanoparticles as described in US 2009/0136585, can also be used. Examples include poly DL-lactide-co-glycolide (PLGA) nanoparticles, e.g., surface-modified with known surface-modifying agents, such as heparin, dodecyl-methylammonium bromide (DMAB), DEAE-Dextran, lipofectin, and fibrinogen (see, e.g. Song et al., J. Control. Release, 54:201-211 (1998); Labhasetwar et al., J. Pharm. Sci., 87:1229-34 (1998); Lee et al., Biomaterials 29(9): 1224-1232 (2008); and US 2009/0136585.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1. Identification of an Uncharacterized, BAT-Enriched Adipokine (Batotin) that is Regulated by Feeding/Fasting We considered the possibility that BAT produces an adipokine to inhibit leptin function. This possibility is strengthened by the phenotypes of fat-selective Hlx transgenic mice[32]. We observed that subcutaneous inguinal WAT (iWAT) depots of Hlx transgenic mice are visibly brown-like and have elevated basal thermogenesis. As a result, under a normal chow diet, the transgenic mice have a 30% increase of daily food intake in order to counteract elevated energy expenditure and maintain a normal body weight[32], indicating that browned WAT produces a signal communicating with hypothalamus to adjust food intake. We thus envisioned that candidates of such an adipokine should 1) have a higher expression in BAT relative to WAT, 2) be induced in iWAT of Hlx transgenic mice, 3) be regulated by feeding/fasting. As outlined in FIG. 1, we analyzed our RNA-Seq datasets, GSE56367[ref. 33] (BAT and WAT of wild type mice) and GSE78143[ref. 32] (iWAT of Hlx transgenic mice and control mice) with a focus on previously uncharacterized genes. Genes picked up from this analysis were then examined with public microarray dataset GSE7623[ref. 34] to see whether any of them is induced by fasting. Finally, we used a bioinformatic tool [Bendtsen et al., Protein Eng. Des. Sel. 17, 349-356 (2004)] to predict whether they are potentially secreted proteins. These combined analyses led to the identification of a previously uncharacterized gene 1190005I06RIK, and its human ortholog C16orf74. The mouse 1190005I06RIK gene has an open reading frame (ORF) of 111 amino acids, while human C16orf74 has an ORF of 76 amino acids (FIG. 2). As described below (see FIG. 5), we found that translation of 1190005I06RIK is in fact initiated from an internal in-frame ATG corresponding to the start codon of human C16orf74, therefore both mouse 1190005I06RIK and human C16orf74 encode an 8 kD polypeptide with 76 amino acid residues. They contain neither a transmembrane domain nor a signal peptide, but are predicted ([Bendtsen et al., Protein Eng. Des. Sel. 17, 349-356 (2004) to be a non-classically secreted protein with a high score (NN-score 0.846 for 1190005I06RIK and 0.868 for C16orf74) that is in line with fibroblast growth factor 1 (Fgf1) (NN-score 0.847). We named this polypeptide as Batotin.

Our RT-qPCR analysis confirmed that Batotin is selectively expressed in adipose tissue and liver, and is enriched in BAT (FIG. 3A). It is present in mature adipocytes, not in preadipocytes (FIG. 3B). Analysis of the public microarray data GSE7623 shows that Batotin was induced by 24-hr fasting in WAT and liver of rats (FIG. 3C). To further validate this, we fasted wild type mice for 12 hr and then re-fed for 2 hr. Batotin mRNA was suppressed by re-feeding in adipose tissue and liver (FIG. 3D). Thus, Batotin expression is regulated by feeding/fasting in a manner that is opposite to that of leptin. We also found that Batotin expression in iWAT was increased by cold exposure (FIG. 3E), consistent with its enrichment in BAT. (Please note, quantitative data presented in all the figures of this application represent mean SEM, *$p < 0.05$, $p < 0.01$, *$p < 0.001$.)

Figures 4A, 4B:
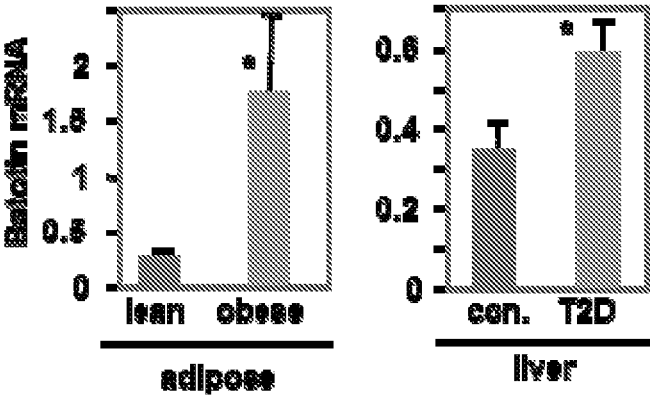
FIGS. 4A-4B. Batotin expression in adipose tissue (A) from 5 obese children and 6 normal weight children (Data from GSE9624), and in liver (B) from 10 type 2 diabetic people (T2D) and 7 normal subjects (con.) (Data from GSE23343).

Example 2. Expression of Batotin in Human Subjects with Obesity and Type 2 Diabetes We conducted a survey of Batotin mRNA expression in public human Affymetrix array datasets. Batotin expression was significantly higher in adipose tissue of obese children compared with normal weight children (GSE9624[ref. 35]) and in liver of people with type 2 diabetes compared with normal subjects (GSE23343[ref. 36]) (FIGS. 4A-4B). Thus, there is a possible correlation of Batotin expression with human obesity and type 2 diabetes.

Figures 5A, 5B:
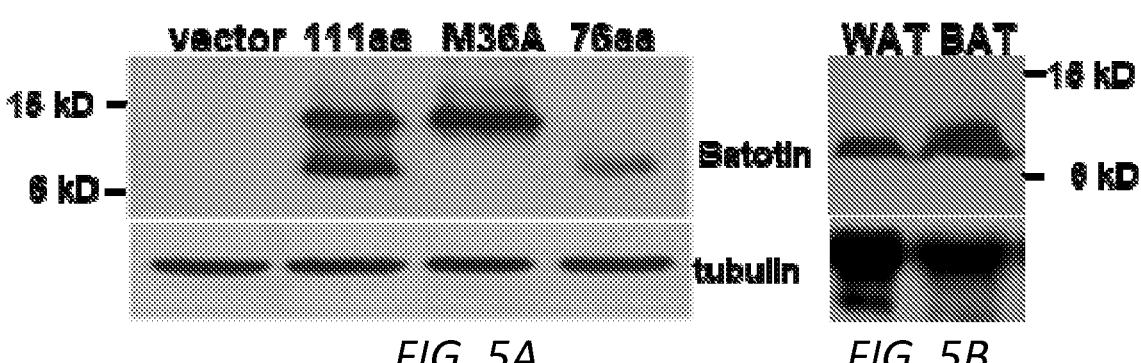
FIGS. 5A-5B. (A) Ecotopic expression of mouse Batotin plasmids as indicted inn HEK293 cells. 111aa: full open reading frame; M36A, internal ATG (Methionine) is mutated; 76 aa, open reading from the internal ATG (B) Endogenous expression of Batotin in BAT and WAT of wild type mice as an 8 kD protein.

Example 3. Mouse Batotin is Translated from an Internal ATG to Produce an 8 kD Polypeptide with 76 Amino Acid Residues As mentioned above, mouse Batotin has an internal in-frame ATG that corresponds to the start codon of human Batotin (76 aa). Moreover, this internal ATG is flanked by a strong kozak sequence (GACGCCATGG (SEQ ID NO:3)). These together raise the possibility of an alternative translation. To test this, we generated mouse Batotin plasmids that express either the whole ORF (111 aa), the whole ORF with the internal ATG mutated (M36A), or the 76 aa fragment from the internal ATG. We obtained an antibody against mouse Batotin (Santa Cruz, Cat #sc-163566), and the peptide antigen used is located immediately downstream of the internal Methionine. We transfected these plasmids into HEK293 cells. As shown in FIG. 5A, the 111 aa ORF produced two bands, 12 kD and 8 kD, which were not present in vector control, validating the specificity of the antibody. Interestingly, the 8 kD band, which migrated at the same position as the product of the 76 aa plasmid, disappeared when the internal ATG was mutated. These results suggest that, in HEK293 cells, the mouse Batotin ORF produces two isoforms, 12 kD and 8 kD, with the latter being translationally initiated from an internal ATG. More importantly, endogenous Batotin protein from adipose tissue and adipocyte culture was produced as an 8 kD band that ran at the same position of the 8 kD produced by HEK293 cell transfection (FIG. 5B and FIG. 6), while no 12 kD band was detected, suggesting that endogenous mouse Batotin is translated from the internal ATG to express the 8 kD polypeptide analogous to human Batotin. Thus, plasmid and adenoviral cDNA constructs encoding the 76 aa polypeptide (8 kD band) are used to express mouse Batotin in this grant application, unless otherwise indicated.

Example 4. Batotin is a Secreted Protein

Batotin is predicted to be a non-classically secreted protein. To directly test this, we cultured immortalized brown preadipocytes and differentiated them into adipocytes. The immortalized brown preadipocyte cell line, after differentiation, has a very high basal expression of Ucp1 and is highly responsive to b3 adrenergic stimulation[33, 37]. We collected serum-free conditioned media from these differentiated adipocytes, and concentrated them with an Amicon filter (3 kD cut-off, Millipore). The 8 kD Batotin, but not the 12 kD band, was detected in both cell extracts and conditioned media (FIG. 6A), whereas tubulin was only present in the cell extracts, suggesting that endogenous Batotin is secreted. Batotin was also secreted into culture media of HEK293 cells when transfected with its plasmid.

Next, we determined whether endogenous Batotin is secreted from BAT tissue. We isolated BAT depots from wild type mice and chopped them into small pieces. After washing with PBS, we incubated them with conditioned media. At different time points, conditioned media were removed completely and new fresh conditioned media were added as indicated in FIG. 6B. Tubulin was present in the conditioned media in the first two hours due to initial tissue breakage, and was almost not detected at the 6-hr time point. In contrast, Batotin, detected as 8 kD, was robustly present at the 6-hr time point (FIG. 6B), indicating an active secretion. These experiments have been independently repeated five times and similar results were obtained. The data strongly suggest that Batotin is a secreted protein.

Example 5. Mouse and Human Batotin Proteins are Present in Circulation

Our western blot analysis of endogenous Batotin protein in circulation of wild type mice has produced inconsistent, both positive and negative results, probably due to the high concentration of total serum protein (60-80 µg/µl) and the relatively low amount of Batotin. To circumvent this problem, we used antibodies against mouse Batotin (Santa Cruz, Cat #sc-163566) and Protein A beads to immunoprecipitate Batotin from serum of wild type mice, and then used the immunoprecipitates for western blot analysis. As shown in FIG. 7A, endogenous Batotin was readily detected in circulation of wild type mice; moreover, a much higher level of circulating Batotin was present in aP2 promoter-driven Batotin transgenic mice we generated. To examine whether Batotin is present in human serum, we obtained an antibody against human Batotin (ThermoFisher, Cat #PA5-61945). We validated this antibody using HEK293 cells expressing human Batotin cDNA plasmids (FIG. 7B). Immunoprecipitation followed by western blot analysis using this antibody led to the detection of Batotin in human serum (FIG. 7C). To further confirm that human Batotin is secreted into circulation, we generated adenovirus containing human Batotin cDNA, and expressed Batotin in liver through tail vein injection. One week after injection, human Batotin was detected in mouse circulation without the need of immunoprecipitation (FIG. 7D). Similar observation was made with adenovirus expressing mouse Batotin cDNA. The results in FIGS. 7A-7D unequivocally showed that both mouse and human Batotin proteins are secreted into circulation.

Example 6. Batotin Suppresses Leptin Signaling in HEK293 Cells

Leptin signaling can be reconstituted in HEK293 cells by expressing the leptin receptor LepRb[38, 39]. We performed similar experiments to examine STAT3 phosphorylation. Antibodies against phosphorylated STAT3 (pTyr705) (Cell Signaling Technology, Cat #CST-9145) and total STAT3 (Cat #CST-9139) have been widely used [e.g., ref 38, 40]. Leptin treatment of HEK293 cells transfected with LepRb elicited STAT3 phosphorylation (pTyr705) (lane 2, FIG. 8A). Strikingly, co-transfection of mouse Batotin (76 aa) or its human ortholog abolished STAT3 phosphorylation (lane 4 and 5). Expression of the whole ORF (111 aa) of mouse Batotin produced similar effects (lane 3). However, since this whole ORF expresses both 12 kD and 8 kD in HEK293 cells (FIG. 5A), it is unclear whether the 12 kD is also functional. Experiments expressing the whole ORF with the internal Methionine mutated should clarify this issue.

Figure 8B:
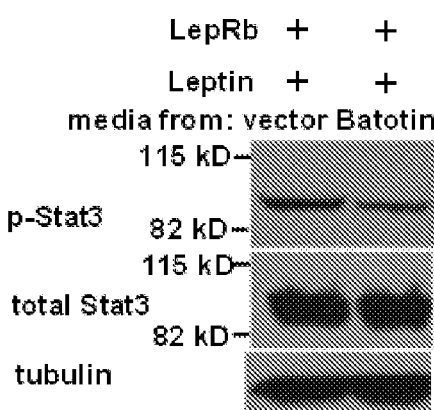

Batotin is secreted into culture media of HEK293 cells when transfected with its plasmid. We collected serum-free conditioned media from this transfection and concentrated, and added into HEK293 cells transfected with LepRb. Compared with control media, conditioned media containing Batotin suppressed STAT3 phosphorylation (FIG. 8B).

Example 7. Recombinant Batotin Protein Suppresses Leptin Signaling

Figure 9A:
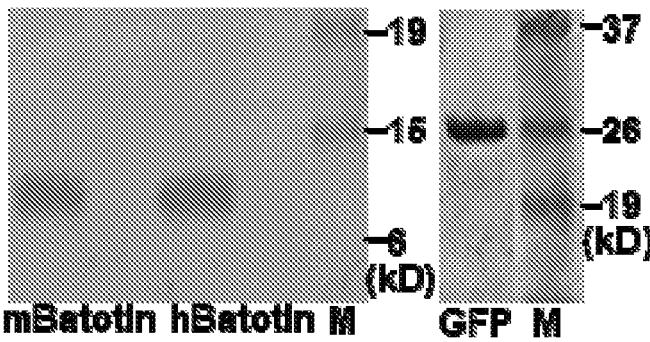
FIGS. 9A-9B. Purified Batotin protein inhibits leptin-induced Stat3 phosphorylation. (A) Mouse and human Batotin protein and GFP protein were produced from *E. coli.* Coommassie Blue staining of purified proteins. (B) HEK293 cells transfected with leptin receptor plasmids were serum-starved. Cells were treated with recombinant Batotin protein or GFP for 20 min, followed by co-incubation with leptin for 30 min. Immunofluorescence staining of phosphorylated Stat3 (Green) and DAPI staining of nuclei (Blue) were performed.
Figure 9B:
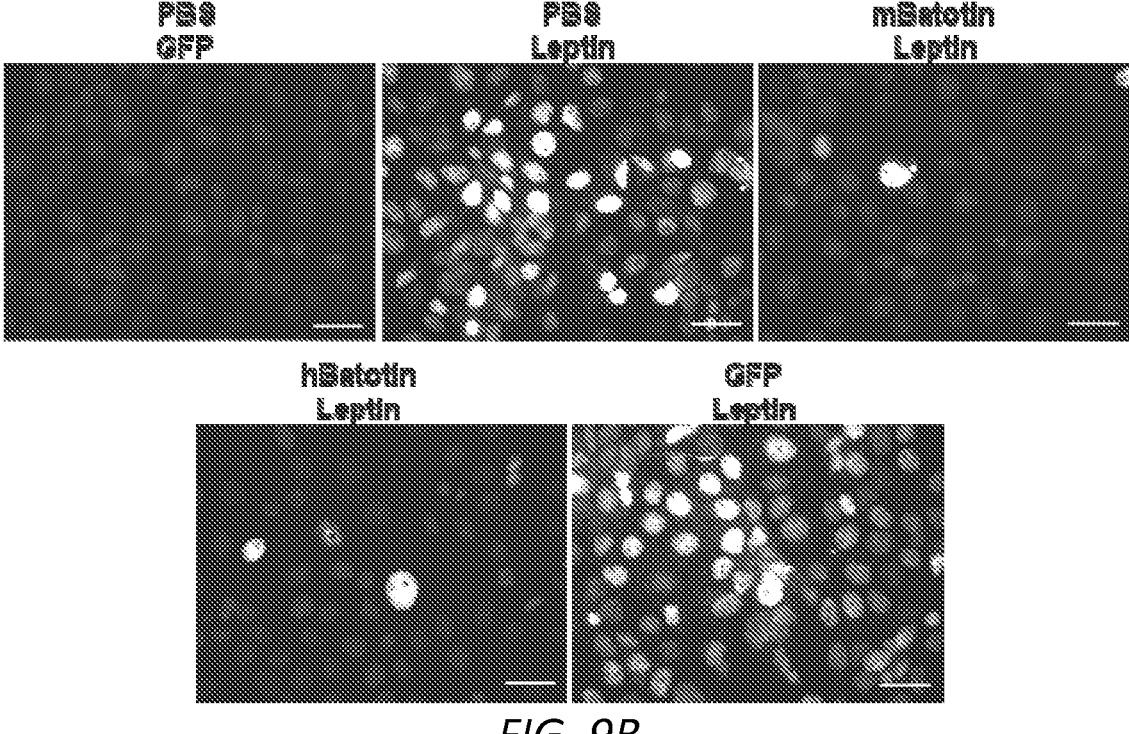

To more rigorously test the inhibitory effect of Batotin on leptin receptor activation, we expressed both mouse and human Batotin protein (mBatotin and hBatotin) with a six-amino-acid His tag at its C-terminus in *E. coli*, and purified Batotin protein with a Ni-NTA column followed by endotoxin removal with a commercial system (Thermo Fisher) (FIG. 9A). His tagged GFP protein was purified as well and used as a control. Addition of leptin into HEK293 cells transfected with leptin receptor led to activation of STAT3 and its nuclear translocation, as revealed by immunofluorescence staining with antibodies against phosphorylated STAT3 (pTyr705) (FIG. 9B). Incubation with recombinant mBatotin or hBatotin blocked leptin-induced STAT3 activation, whereas GFP protein had no effect (FIG. 9B). By quantification, we found that more than 80% of cells treated with leptin contained a p-STAT3 positive (including weak staining) nucleus; this number was reduced to less than 10% by addition of Batotin protein. These results provide compelling evidence that Batotin acts extracellularly to inhibit leptin signaling.

Example 8. Recombinant Batotin Binds to Leptin Receptor

Figure 10:
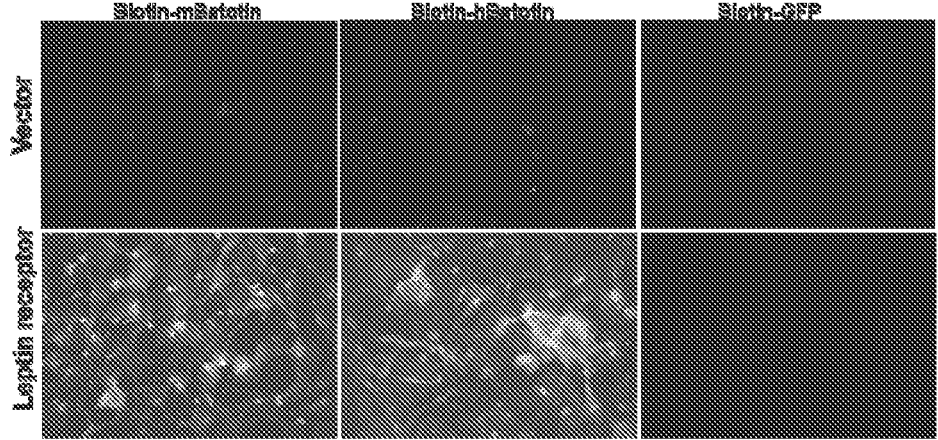
FIG. 10. Leptin receptor-dependent binding of Batotin to HEK293 cell surface. Cells transfected with either vector (top row) or leptin receptor (LepRb) (bottom row) plasmids were incubated with biotin-labeled recombinant Batotin protein or GFP for 30 min. After extensive washing, cells were visualized with Alexa Fluor 488 Streptavidin without permeabilization.

Data presented in FIG. 9 raise the possibility that Batotin might bind to leptin receptor. To test this, we labeled recombinant mBatotin, hBatotin and GFP protein with biotin using the Biotinylation Sulfo-NHS kit (ThermoFisher, CAS #119616-38-5), and free biotin was removed through filtration. Biotin-labeled Batotin and GFP were incubated with HEK293 cells transfected with either leptin receptor or vector plasmids. After extensive washing, staining with Alexa Fluor 488 Streptavidin (ThermoFisher, #5-11223) revealed that both mBatotin and hBatotin, but not GFP, bound to cell surface in a leptin receptor-dependent manner (FIG. 10). Moreover, this binding was abolished by pre-incubation with leptin. Please note, in order to examine cell surface staining, cells were not permeabilized; hence DAPI staining was not performed, but cells with confluency were used in all treatments. The results suggest that Batotin binds to leptin receptor. However, it is currently unclear whether Batotin and leptin compete for the same binding pocket, or Batotin binds to a distinct pocket and such a binding can be prevented in the presence of leptin.

Example 9. Circulating Batotin is Able to Get into Hypothalamus

Figures 11A, 11B:
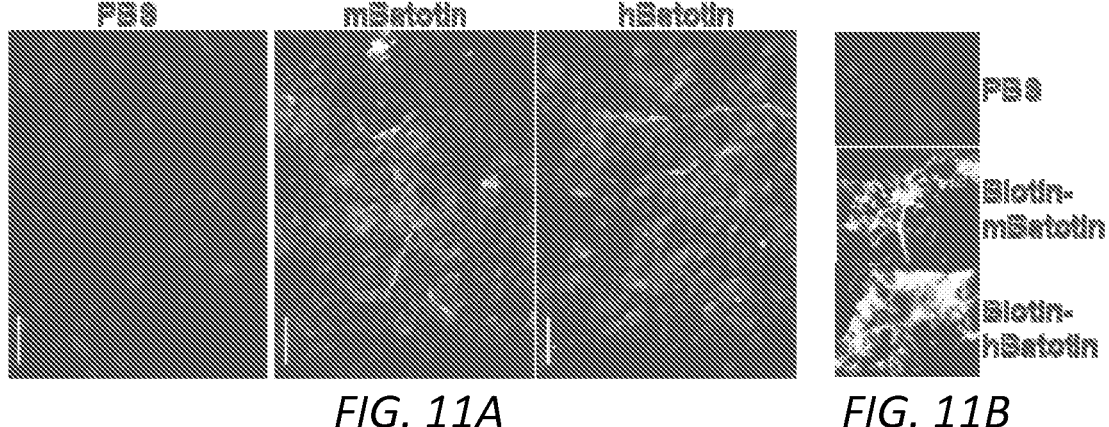
FIGS. 11A-11B. Batotin protein is able to get into hypothalamus. (A) Batotin protein (25 μg/mouse) was tail vein-injected. Slices of hypothalamus were immunostained with antibodies against either mouse Batotin (left and middle panels) or human Batotin (right panel). (B) Biotin-labeled Batotin protein (25 μg/mouse) was tail vein-injected. Slices of hypothalamus were stained with Alexa Fluor 488 Streptavidin. In both (A) and (B), Green, Batotin; Blue, DAPI.

We tail vein-injected recombinant Batotin protein into mouse circulation. 3 hr after injection, mice were terminally anesthetized and transcardially perfused with PBS. Hypothalamus was carefully dissected out, and frozen slices were prepared and stained with antibodies against either mouse Batotin or human Batotin. As shown in FIG. 11A, recombinant mBatotin and hBatotin can be detected in hypothalamus. To further validate this finding, we tail vein-injected biotin-labeled Batotin. Staining of hypothalamic slices with Alexa Fluor 488 Streptavidin revealed presence of biotin-labeled Batotin (FIG. 11B). Thus, Batotin in the circulation can cross the blood-brain barrier and get into hypothalamus.

Example 10. Batotin Transgenic Mice are Hyperphagia and Morbidly Obese

Figure 12A:
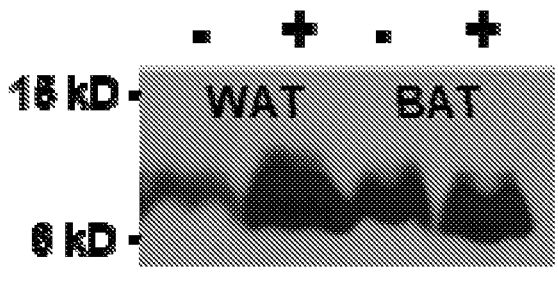
FIGS. 12A-12D. aP2-Batotin transgenic mice are hyperphagia and obese. (A) Batotin expression in wild type (−) and transgenic mice (+). (B-C) Body weights of male mice on chow diets, n=12-13 mice/group. (D) Accumulative consumption of chow diets (measurements were started when mice are 4-week-old), n=10-11 mice/group. Inset shows accumulative food consumption at Day 2 and Day 9 of the experiments. Increased food intake was observed when there was no body weight difference compared with control littermates, suggesting hyperphagia is not due to body weight.
Figure 12B:
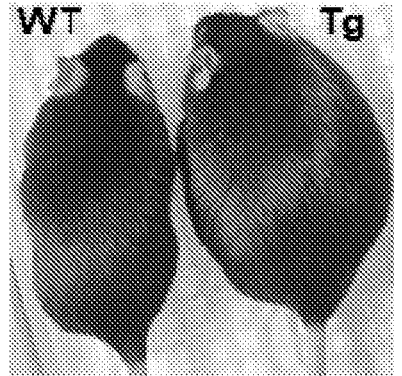
Figure 12C:
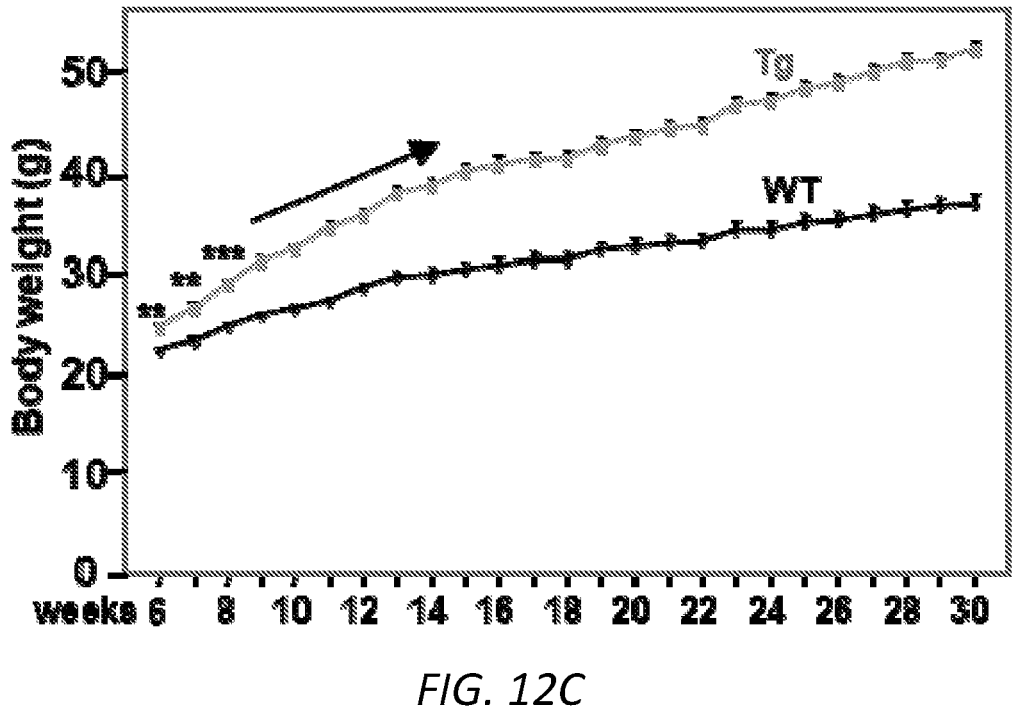

To test our hypothesis in vivo, we generated aP2-Batotin transgenic mice. The transgene was expressed in both BAT and WAT (FIG. 12A). Before weaning (3- to 4-week old), there was no body weight difference between the transgenic mice and control littermates. After weaning, the transgenic mice displayed a rapid increase of body weight. As shown in FIGS. 12B and 12C, at 7-month-old, the male transgenic mice became overly obese and weighed 52.32±0.81 g, and the control mice weighed 36.74±1.0 g, representing a 42% increase of body weight. Similarly, female transgenic mice had a 40% increase of body weight. All these occurred under a normal chow diet. Importantly, we have several independent Batotin transgenic founder lines, and they all show a significantly higher body weight, thus excluding the possibility that the phenotype is due to disruption of a genomic locus.

Figure 12D:
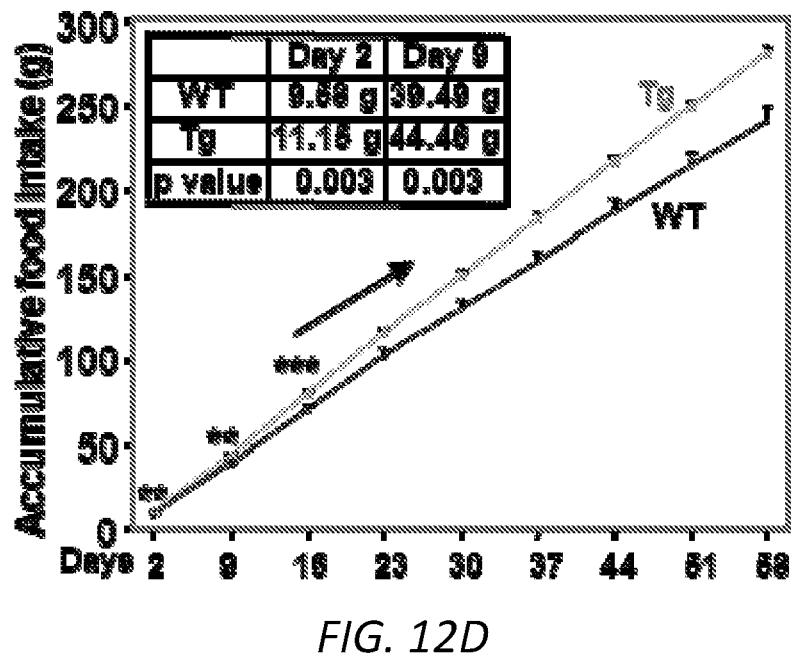

We measured their food intake. We started the experiments when the mice were 4-week-old, a time point that no body weight difference was observed. We found that the transgenic mice had a significantly higher food intake at the beginning (inset of FIG. 12D) and throughout the experiments (FIG. 12D) with an average of 0.7 g more per day (p=0.00018), suggesting that increased food consumption is not due to body weight. The data clearly showed that the Batotin transgenic mice are hyperphagia, causing their obese phenotype.

Figure 13A:
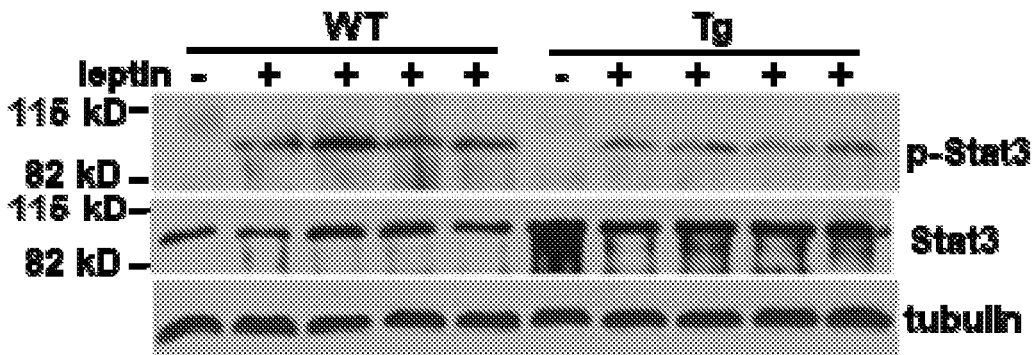
FIGS. 13A-C. (A) STAT3 phosphorylation in hypothalamus of mice i.p. injected with leptin (1 mg/kg body weight). (B) Circulating glucose, leptin and insulin after 5-hr fasting in 6-week-old mice (n=7 mice/group). (C) Circulating glucose, leptin and insulin after 5-hr fasting in 9-month-old mice (n=10-12 mice/group). Grey bar, wild type mice; blue bar, transgenic mice. The data showed that leptin resistance precedes obesity in the transgenic mice, further suggesting that Batotin directly antagonizes leptin signaling.
Figure 13B:
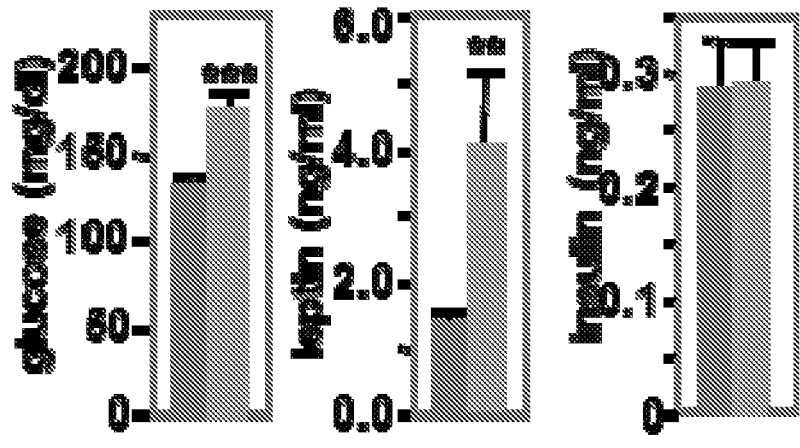
Figure 13C:
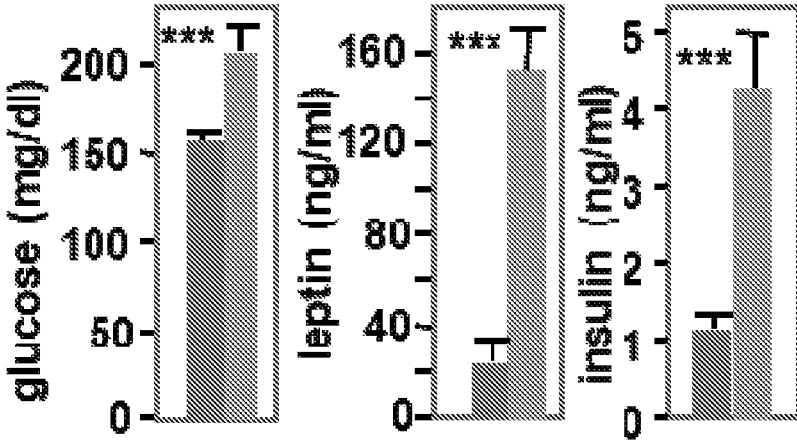

Example 11. Batotin Transgenic Mice Display Impaired Leptin Signaling and have Higher Blood Glucose Level and Leptin Level Our experiments performed in HEK293 cells suggest that Batotin suppresses leptin signaling (FIG. 8-11). We determined whether this can be recapitulated in vivo. We i.p. injected leptin (1 mg/kg body weight) into Batotin transgenic mice and control littermates. We isolated hypothalamus 45 min after injection. We observed decreased STAT3 phosphorylation in the transgenic mice at both age points examined, 9-week-old and 19-week-old (FIG. 13A). Thus, expression of Batotin in adipose tissue interferes with hypothalamic leptin signaling, underlying the observed hyperphagia and obese phenotypes. These results provide strong in vivo support to our hypothesis. Impaired leptin signaling in hypothalamus is expected to increase blood glucose and leptin levels independent of body weight. Indeed, levels of glucose and leptin, but not insulin, were significantly elevated in Batotin transgenic mice at 6-week-old when little body weight difference was observed (FIG. 13B), providing further evidence that impaired leptin signaling is a primary defect in the transgenic mice. As expected, these parameters as well as insulin level became deteriorated in old transgenic mice (FIG. 13C). Leptin mRNA expression in adipose tissue are similar between the transgenic mice and control mice.

Example 12. Pair-Feeding Prevents Obesity of the Batotin Transgenic Mice

Figures 14A, 14B:
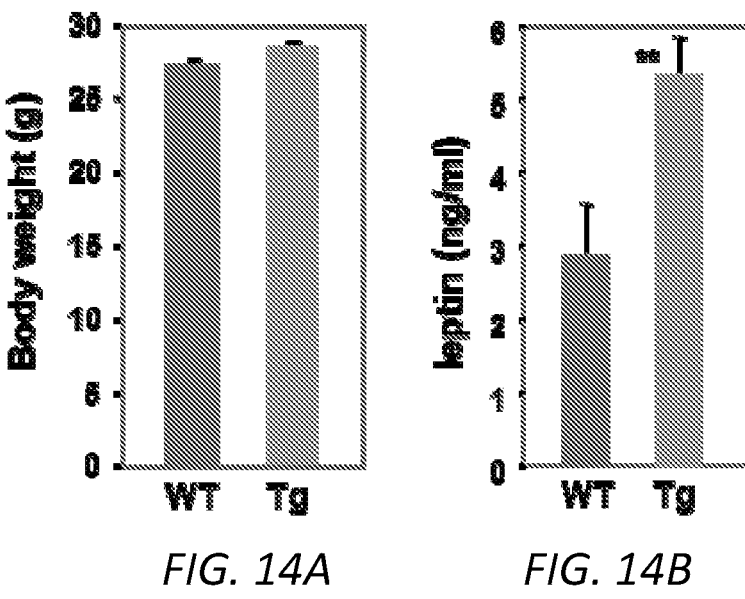
FIGS. 14A-14B. (A) Body weights of Batotin transgenic mice (n=9) and control littermates (n=6) at 17-week-old. Pair-feeding for transgenic mice was started when mice were 8-weeks-old. (B) Circulating leptin level at 17-week-old.

To further validate that the obese phenotype of the Batotin transgenic mice was caused by hyperphagia, we performed pair-feeding experiments in which the amounts of food given to the transgenic mice were identical to those consumed by the control mice. As shown in FIG. 14A, after 9-week pair feeding, the transgenic mice had a similar body weight as control mice. Despite normalization of body weight, these transgenic mice still retained elevated circulating leptin level (FIG. 14B), again indicating a primary defect of leptin signaling in the transgenic mice.

Figure 15A:
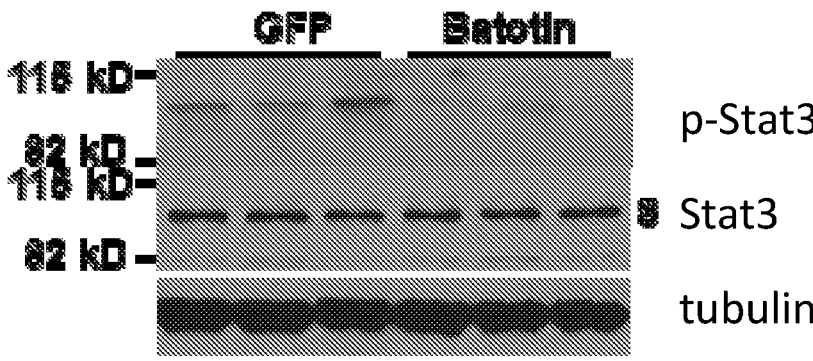
FIGS. 15A-15B. Adenoviruses expressing Batotin or GFP were tail vein-injected into 12-week-old male mice. (A) Hypothalamic Stat3 phosphorylation after leptin injection. (B) Glucose and leptin levels after 5-hr fasting. Grey bar, GFP; blue bar, Batotin. n=5 mice/group.
Figure 15B:
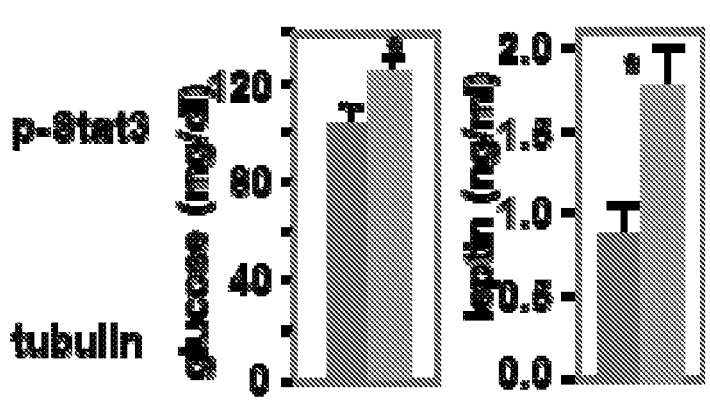

Example 13. Acute Hepatic Expression of Batotin Through Adenoviral Injection Causes Hypothalamic Leptin Resistance As an alternative approach to examine the effect of Batotin on leptin signaling, we tail vein-injected adenovirus to acutely express Batotin in the liver of wild type mice. One week after viral expression, the mice were i.p. injected with leptin (1 mg/kg body weight). As shown in FIGS. 15A-15B, compared with control mice injected with the same number of GFP adenoviral particles, hepatic expression of Batotin suppressed leptin-stimulated STAT3 phosphorylation in hypothalamus, and elevated circulating glucose and leptin levels, reminiscent of what observed in Batotin transgenic mice. These results further suggest that Batotin acts in an endocrine manner to suppress leptin signaling.

Figure 16A:
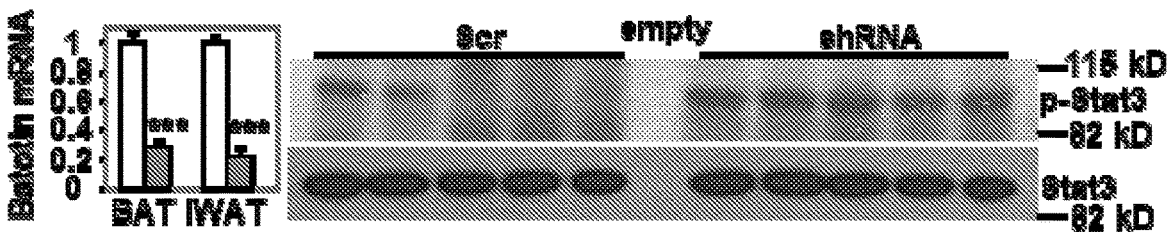
FIGS. 16A-16B. Adenoviral knockdown of Batotin in BAT and iWAT (A) or in liver (B) increases leptin-induced Stat3 phosphorylation in hypothalamus. (A) 3-month-old female mice. (B) 3-month-old male mice. White bar, scramble; Grey bar, Batotin shRNA.
Figure 16B:
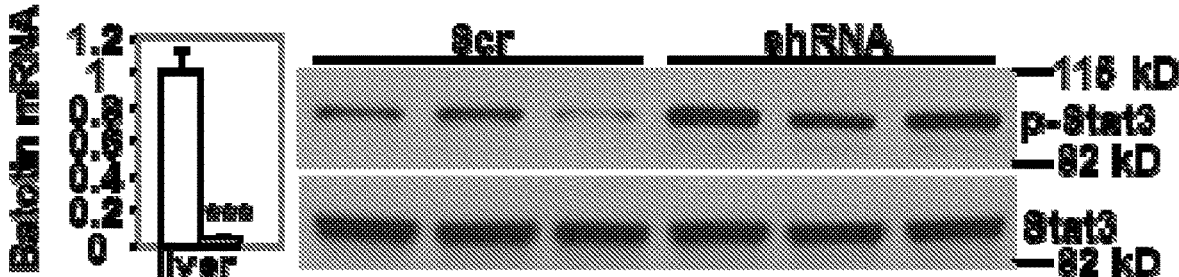

Example 14. Acute Knockdown of Batotin in Adipose or Liver Enhances Leptin Signaling To test the effect of loss of Batotin on leptin signaling, we directly injected Batotin knockdown adenovirus into BAT and iWAT at $1\times10^{10}$ transducing units per injection, as described[41, 42]. The BAT pad received 2 injections, and iWAT received 6 injections for each pad. One week after viral injection, mice were fasted overnight and i.p. injected with leptin. The adenoviral knockdown reduced Batotin mRNA expression by 70%, which led to increased STAT3 phosphorylation in hypothalamus (FIG. 16A). Despite low expression of Batotin in liver, its induction by fasting and the considerable liver mass promoted us to knockdown hepatic Batotin through tail vein injection of adenovirus. Liver Batotin mRNA was reduced by 90%, resulting in increased leptin-stimulated STAT3 phosphorylation (FIG. 16B). These results suggest a physiological role of endogenous Batotin in regulation of leptin signaling. Please note, data of FIG. 15 and FIG. 16 have been replicated with a second cohort of mice.

Example 15. Generation of Batotin Conditional Knockout Mice

Figure 17:
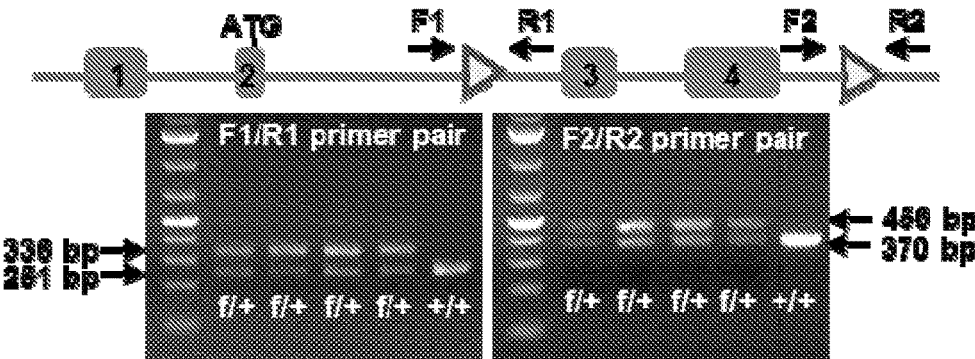
FIG. 17. Genotyping of Batotin conditional KO mice (F1). Batotin has 76 aa, and Exon 3 and 4 encode 67 aa. Exon 3 and 4 were floxed by two loxP sites. Germline transmissible conditional mice were obtained. The conditional mice will be used to delete Batotin in adipose and/or liver.

The previous Batotin knockout ES clones failed to produce knockout mouse strain. We thus designed a new targeting construct. Batotin locus has 4 exons. Exon 2 encodes the first 9 aa, and exon 3 and 4 encode the reminder 67 aa. Two LoxP sites were inserted to flank exon 3 and 4 (FIG. 17), which, upon crossing with Cre mice, will delete exon 3 and 4 (67 aa). From germ line-transmissible positive founder lines (F0), we recently obtained heterozygous F1 conditional (one allele is floxed, f/+) mice, which have been confirmed by genotyping PCR, southern blot, and sequencing (FIG. 17). The f/+ mice are now being used to generate f/f mice with tissue-specific Cre.

Example 16. Subcutaneous Fat Transplantation from Batotin Transgenic Mice to Wild Type Mice To demonstrate that secreted Batotin from adipose tissue of the transgenic mice is responsible for their phenotype, adipose transplantation experiments are performed. Subcutaneous inguinal fat will be obtained from the transgenic mice and control littermates (as control). Fat depots are cut into 100 mg per pieces. Each recipient mouse is grafted with 1 g fat tissue. A long incision is made across the lower back of 10-week-old wild type mice so that fat pieces will be essentially laid out to come in direct contact with the skin/endogenous subcutaneous fat, as described[51]. Animals, after recovery from surgery, are monitored for food intake and body weight gain. Increases of food consumption and body weight gain in mice grafted with fat from transgenic mice support our model. Both male and female recipient groups (n=10 mice/group) are used.

Example 17. Hepatic Adeno-Associated Viral Expression of Batotin

Secreted Batotin from liver through adenoviral expression regulates leptin signaling (FIG. 15). To determine its long-term effect, adeno-associated virus (AAV) serotype 8 is used to chronically express Batotin gene in liver. Both male and female groups are used in experiments. We have cloned Batotin gene into AAV8 vector downstream of human thyroid hormone-binding globulin (TBG) promoter, which allows liver-specific gene expression. We co-transfect this plasmid along with the packaging plasmid and helper plasmid into HEK293 cells to produce AAV virus[52]. Virus is purified using gradient centrifugation and tittered by qPCR. Batotin-AAV ($3\times10^{11}$ genomic copy/mouse) is tail vein injected into 3-month-old wild type mice (n=10/group). Mice injected with GFP-AAV are used as a control group. Body weight, food intake, and levels of blood glucose, leptin, insulin and Batotin are followed under both normal chow and high fat diets. These experiments should recapitulate the phenotypes of the transgenic mice, and provide further evidence that Batotin secreted by peripheral tissue controls appetite and body weight.

Example 18. Recombinant Batotin Protein Injection

Recombinant Batotin protein (both mBatotin and hBatotin) is injected subcutaneously at different doses (5 to 30 µg per mouse per day) along with leptin (1 mg/kg body weight) or PBS into wild type mice (n=5 per group). Hypothalamus will be collected 45 min after injection, and leptin-induced STAT3 phosphorylation will be measured. Batotin protein injection may lead to a dose-dependent inhibition of STAT3 phosphorylation.

After an effective dosage is established, we subcutaneously inject Batotin or GFP protein daily into wild type mice for up to three weeks, depending on the injection dosage. Both male and female groups (10 mice/group) are used. We examine the effects of Batotin protein on food intake and body weight gain, and blood glucose and leptin levels.

Example 19. Metabolic Phenotypes of Batotin Knockout Mice

The in vivo data from Batotin knockdown experiments (FIG. 16) strongly support a physiological role of endogenous Batotin in modulation of leptin signaling. The Batotin conditional (f/f) mice are crossed with Adiponectin-Cre mice[54] (C57BL6 background, obtained from Dr. Evan Rosen's lab) to generate adipose-specific knockout (FKO) mice and control littermates (f/f). We examine STAT3 phosphorylation in hypothalamus by western blot and immunofluorescence staining at both basal (no fasting) condition and leptin stimulated condition (after a 16-hr fasting). We examine hypothalamic mRNA expression of neuronal peptides POMC, AGRP and NPY. We measure short-term food intake in response to leptin injection as described above (aim 2). The FKO mice may become more leptin-sensitive, showing increased hypothalamic leptin receptor activation and a further reduction of food intake in response to leptin.

Next, mice are fed with either a normal chow diet or a high fat diet (HFD) [36% (w/w) fat, Bioserv #F3282], and accumulative food intake and body weight gain are followed for at least 3 months. Blood glucose, leptin, insulin, and Batotin levels are measured. At the end of HFD experiments, leptin is i.p. injected to further examine leptin sensitivity at HFD-induced obese state. Both male and female groups are used with 10 mice/group. The FKO mice may have decreased food intake and lower blood glucose level, and retain leptin sensitivity after HFD.

REFERENCES CITED

1. Stanley, S., Wynne, K., McGowan, B. & Bloom, S. Hormonal regulation of food intake. Physiological reviews 85, 1131-1158 (2005).
2. Coll, A. P., Farooqi, I. S. & O'Rahilly, S. The hormonal control of food intake. Cell 129, 251-262 (2007).
3. Mosialou, I. et al. MC4R-dependent suppression of appetite by bone-derived lipocalin 2. Nature 543, 385-390 (2017).
4. Williams, K. W. & Elmquist, J. K. From neuroanatomy to behavior: central integration of peripheral signals regulating feeding behavior. Nature neuroscience 15, 1350-1355 (2012).
5. Ge, X. et al. LEAP2 Is an Endogenous Antagonist of the Ghrelin Receptor. Cell metabolism 27, 461-469 e466 (2018).
6. Cui, H., Lopez, M. & Rahmouni, K. The cellular and molecular bases of leptin and ghrelin resistance in obesity. Nature reviews. Endocrinology (2017).
7. Duerrschmid, C. et al. Asprosin is a centrally acting orexigenic hormone. Nature medicine 23, 1444-1453 (2017).
8. Coppari, R. & Bjorbaek, C. Leptin revisited: its mechanism of action and potential for treating diabetes. Nature reviews. Drug discovery 11, 692-708 (2012).
9. Dalamaga, M. et al. Leptin at the intersection of neuroendocrinology and metabolism: current evidence and therapeutic perspectives. Cell metabolism 18, 29-42 (2013).
10. Flak, J. N. & Myers, M. G., Jr. Minireview: CNS Mechanisms of Leptin Action. Molecular endocrinology 30, 3-12 (2016).
11. Morton, G. J., Meek, T. H. & Schwartz, M. W. Neurobiology of food intake in health and disease. Nature reviews. Neuroscience 15, 367-378 (2014).
12. Myers, M. G., Jr., Munzberg, H., Leininger, G. M. & Leshan, R. L. The geometry of leptin action in the brain: more complicated than a simple ARC. Cell metabolism 9, 117-123 (2009).
13. Zhang, Y. et al. Positional cloning of the mouse obese gene and its human homologue. Nature 372, 425-432 (1994).
14. Tartaglia, L. A. et al. Identification and expression cloning of a leptin receptor, OB-R. Cell 83, 1263-1271 (1995).
15. Yu, X., Park, B. H., Wang, M. Y., Wang, Z. V. & Unger, R. H. Making insulin-deficient type 1 diabetic rodents thrive without insulin. Proceedings of the National Academy of Sciences of the United States of America 105, 14070-14075 (2008).
16. Fujikawa, T., Chuang, J. C., Sakata, I., Ramadori, G. & Coppari, R. Leptin therapy improves insulin-deficient type 1 diabetes by CNS-dependent mechanisms in mice. Proceedings of the National Academy of Sciences of the United States of America 107, 17391-17396 (2010).
17. Huo, L. et al. Leptin-dependent control of glucose balance and locomotor activity by POMC neurons. Cell metabolism 9, 537-547 (2009).
18. Coppari, R. et al. The hypothalamic arcuate nucleus: a key site for mediating leptin's effects on glucose homeostasis and locomotor activity. Cell metabolism 1, 63-72 (2005).
19. Cummings, B. P. et al. Subcutaneous administration of leptin normalizes fasting plasma glucose in obese type 2 diabetic UCD-T2DM rats. Proceedings of the National Academy of Sciences of the United States of America 108, 14670-14675 (2011).
20. Shimomura, I., Hammer, R. E., Ikemoto, S., Brown, M. S. & Goldstein, J. L. Leptin reverses insulin resistance and diabetes mellitus in mice with congenital lipodystrophy. Nature 401, 73-76 (1999).
21. Petersen, K. F. et al. Leptin reverses insulin resistance and hepatic steatosis in patients with severe lipodystrophy. The Journal of clinical investigation 109, 1345-1350 (2002).
22. Oral, E. A. et al. Leptin-replacement therapy for lipodystrophy. The New England journal of medicine 346, 570-578 (2002).
23. Fukuda, M., Williams, K. W., Gautron, L. & Elmquist, J. K. Induction of leptin resistance by activation of cAMP-Epac signaling. Cell metabolism 13, 331-339 (2011).
24. Ozcan, L. et al. Endoplasmic reticulum stress plays a central role in development of leptin resistance. Cell metabolism 9, 35-51 (2009).
25. Rosen, E. D. & Spiegelman, B. M. What we talk about when we talk about fat. Cell 156, 20-44 (2014).
26. Harms, M. & Seale, P. Brown and beige fat: development, function and therapeutic potential. Nat Med 19, 1252-1263 (2013).
27. Kajimura, S., Spiegelman, B. M. & Seale, P. Brown and Beige Fat: Physiological Roles beyond Heat Generation. Cell Metab 22, 546-559 (2015).
28. Cannon, B. & Nedergaard, J. Brown adipose tissue: function and physiological significance. Physiol Rev 84, 277-359 (2004).
29. Lowell, B. B. & Spiegelman, B. M. Towards a molecular understanding of adaptive thermogenesis. Nature 404, 652-660 (2000).
30. Long, J. Z. et al. The Secreted Enzyme PM20D1 Regulates Lipidated Amino Acid Uncouplers of Mitochondria. Cell 166, 424-435 (2016).
31. Wang, G. X. et al. The brown fat-enriched secreted factor Nrg4 preserves metabolic homeostasis through attenuation of hepatic lipogenesis. Nat Med 20, 1436-1443 (2014).
32. Huang, L. et al. Transcription factor Hlx controls a systematic switch from white to brown fat through Prdm16-mediated co-activation. Nature communications 8, 68 (2017).
33. Pan, D. et al. Jmjd3-Mediated H3K27me3 Dynamics Orchestrate Brown Fat Development and Regulate White Fat Plasticity. Developmental cell 35, 568-583 (2015).
34. Nakai, Y. et al. Up-regulation of genes related to the ubiquitin-proteasome system in the brown adipose tissue of 24-h-fasted rats. Bioscience, biotechnology, and biochemistry 72, 139-148 (2008).
35. Aguilera, C. M. et al. Genome-wide expression in visceral adipose tissue from obese prepubertal children. International journal of molecular sciences 16, 7723-7737 (2015).
36. Misu, H. et al. A liver-derived secretory protein, selenoprotein P, causes insulin resistance. Cell metabolism 12, 483-495 (2010).

37. Pan, D., Fujimoto, M., Lopes, A. & Wang, Y. X. Twist-1 is a PPARdelta-inducible, negative-feedback regulator of PGC-1 alpha in brown fat metabolism. Cell 137, 73-86 (2009).

38. Rousso-Noori, L. et al. Protein tyrosine phosphatase epsilon affects body weight by downregulating leptin signaling in a phosphorylation-dependent manner. Cell metabolism 13, 562-572 (2011).

39. Ren, D., Li, M., Duan, C. & Rui, L. Identification of SH2-B as a key regulator of leptin sensitivity, energy balance, and body weight in mice. Cell metabolism 2, 95-104 (2005).

40. Lee, J. et al. Withaferin A is a leptin sensitizer with strong antidiabetic properties in mice. Nature medicine 22, 1023-1032 (2016).

41. Kusminski, C. M., Park, J. & Scherer, P. E. MitoNEET-mediated effects on browning of white adipose tissue. Nature communications 5, 3962 (2014).

42. Rajbhandari, P. et al. IL-10 Signaling Remodels Adipose Chromatin Architecture to Limit Thermogenesis and Energy Expenditure. Cell 172, 218-233 e217 (2018).

43. Christopoulos, A. Allosteric binding sites on cell-surface receptors: novel targets for drug discovery. Nature reviews. Drug discovery 1, 198-210 (2002).

44. Iserentant, H. et al. Mapping of the interface between leptin and the leptin receptor CRH2 domain. Journal of cell science 118, 2519-2527 (2005).

45. Wauman, J., Zabeau, L. & Tavernier, J. The Leptin Receptor Complex: Heavier Than Expected? Frontiers in endocrinology 8, 30 (2017).

46. Peelman, F., Zabeau, L., Moharana, K., Savvides, S. N. & Tavernier, J. 20 years of leptin: insights into signaling assemblies of the leptin receptor. The Journal of endocrinology 223, T9-23 (2014).

47. Pritchard, L. E. et al. Agouti-related protein (83-132) is a competitive antagonist at the human melanocortin-4 receptor: no evidence for differential interactions with pro-opiomelanocortin-derived ligands. The Journal of endocrinology 180, 183-191 (2004).

48. Scott, M. M. et al. Leptin targets in the mouse brain. The Journal of comparative neurology 514, 518-532 (2009).

49. Leinninger, G. M. et al. Leptin acts via leptin receptor-expressing lateral hypothalamic neurons to modulate the mesolimbic dopamine system and suppress feeding. Cell metabolism 10, 89-98 (2009).

50. Cohen, P. et al. Selective deletion of leptin receptor in neurons leads to obesity. The Journal of clinical investigation 108, 1113-1121 (2001).

51. Stanford, K. I. et al. A novel role for subcutaneous adipose tissue in exercise-induced improvements in glucose homeostasis. Diabetes 64, 2002-2014 (2015).

52. Mueller, C., Ratner, D., Zhong, L., Esteves-Sena, M. & Gao, G. Production and discovery of novel recombinant adeno-associated viral vectors. Current protocols in microbiology Chapter 14, Unit14D 11 (2012).

53. Loh, K. et al. Elevated hypothalamic TCPTP in obesity contributes to cellular leptin resistance. Cell metabolism 14, 684-699 (2011).

54. Eguchi, J. et al. Transcriptional control of adipose lipid handling by IRF4. Cell metabolism 13, 249-259 (2011).

55. Postic, C. et al. Dual roles for glucokinase in glucose homeostasis as determined by liver and pancreatic beta cell-specific gene knock-outs using Cre recombinase. The Journal of biological chemistry 274, 305-315 (1999).

56. Ravussin, Y., Xiao, C., Gavrilova, O. & Reitman, M. L. Effect of intermittent cold exposure on brown fat activation, obesity, and energy homeostasis in mice. PloS one 9, e85876 (2014).

57. Bauwens, J. D. et al. Cold tolerance, cold-induced hyperphagia, and nonshivering thermogenesis are normal in alpha(1)-AMPK-/- mice. American journal of physiology. Regulatory, integrative and comparative physiology 301, R473-483 (2011).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating, or reducing risk of, a disorder associated with obesity, or improving glycemic control, in a mammalian subject, the method comprising administering a therapeutically effective amount of an inhibitory nucleic acid that is 10 to 50 nucleotides in length and binds to and inhibits expression of a batotin nucleic acid of SEQ ID NO:8 to a subject in need thereof, wherein the inhibitory nucleic acid is an antisense oligonucleotide, a short interfering RNA (siRNA), or a short, hairpin RNA (shRNA), and wherein the inhibitory nucleic acid comprises a sequence of 10 to 50 nucleotides that is 100% complementary to 10 to 50 nucleotides consecutive nucleotides of SEQ ID NO:8.

2. The method of claim 1, wherein the disorder associated with obesity is diabetes, metabolic syndrome, fatty liver disease, or non-hepatic steatosis.

3. The method of claim 1, wherein the subject has a BMI of at least 25, or at least 30.

4. The method of claim 1, wherein the subject is human.

5. The method of claim 1, wherein the inhibitory nucleic acid is administered parenterally.

6. The method of claim 5, wherein the inhibitory nucleic acid is administered intravenously, intramuscularly, or subcutaneously.

7. The method of claim 1, wherein the inhibitory nucleic acid comprises one or more modified bases or backbone.

8. The method of claim 1, wherein the inhibitory nucleic acid is a gapmer, mixmer, or locked nucleic acid (LNA).

9. The method of claim 1, wherein the disorder associated with obesity is diet-induced obesity.

10. A method of decreasing body weight or fat in a mammalian subject in need thereof, the method comprising administering a therapeutically effective amount of an inhibitory nucleic acid that is 10 to 50 nucleotides in length and binds to and inhibits expression of a batotin nucleic acid of SEQ ID NO:8 to a subject in need thereof, wherein the inhibitory nucleic acid is an antisense oligonucleotide, a short interfering RNA (siRNA), or a short, hairpin RNA (shRNA), and wherein the inhibitory nucleic acid comprises a sequence of 10 to 50 nucleotides that is 100% complementary to 10 to 50 nucleotides consecutive nucleotides of SEQ ID NO:8.

11. The method of claim 10, wherein the subject has a BMI of at least 25, or at least 30.

12. The method of claim 10, wherein the subject is human.

13. The method of claim 10, wherein the inhibitory nucleic acid is administered parenterally.

14. The method of claim 13, wherein the inhibitory nucleic acid is administered intravenously, intramuscularly, or subcutaneously.

15. The method of claim 10, wherein the inhibitory nucleic acid comprises one or more modified bases or backbone.

16. The method of claim 10, wherein the inhibitory nucleic acid is a gapmer, mixmer, or locked nucleic acid (LNA).

* * * * *

SEQUENCE LISTING

```
<160> NUMBER OF SEQ ID NOS: 8

<210> SEQ ID NO 1
<211> LENGTH: 111
<212> TYPE: PRT
<213> ORGANISM: Mus musculus

<400> SEQUENCE: 1

Met Thr Pro Ala Ala His Gly Cys Lys Arg Val Ala Trp Cys Pro Ser
1               5                   10                  15

Arg Pro Pro Ala Ser Ala Pro Ser Ala Pro Gln Glu Ala Ala Arg Arg
            20                  25                  30

Gly Asp Ala Met Gly Leu Lys Pro Ser Cys Leu Lys Gly Phe Lys Met
        35                  40                  45

Cys Val Ser Ser Ser Asn Asn Asn His Asp Glu Ala Pro Val Leu Asn
        50                  55                  60

Asp Lys His Leu Ser Val Pro Asn Ile Ile Ile Thr Pro Pro Thr Pro
65                  70                  75                  80

Thr Gly Met Gly Leu Ser Arg Asp Ser Asn Lys Gln Val Trp Met Asp
```

```
                    85                  90                  95

Glu Leu Gly Ser Tyr Gln Asp Asp Gly Glu Leu Glu Pro Glu Ala
            100                 105                 110

<210> SEQ ID NO 2
<211> LENGTH: 76
<212> TYPE: PRT
<213> ORGANISM: Homo sapiens

<400> SEQUENCE: 2

Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
            20                  25                  30

Leu Asp Val Pro Asp Ile Ile Ile Thr Pro Pro Thr Pro Thr Gly Met
        35                  40                  45

Met Leu Pro Arg Asp Leu Gly Ser Thr Val Trp Leu Asp Glu Thr Gly
    50                  55                  60

Ser Cys Pro Asp Asp Gly Glu Ile Asp Pro Glu Ala
65                  70                  75

<210> SEQ ID NO 3
<211> LENGTH: 10
<212> TYPE: DNA
<213> ORGANISM: Artificial
<220> FEATURE:
<223> OTHER INFORMATION: strong kozak

<400> SEQUENCE: 3
gacgccatgg                                                          10

<210> SEQ ID NO 4
<211> LENGTH: 76
<212> TYPE: PRT
<213> ORGANISM: Pan troglodytes

<400> SEQUENCE: 4

Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
            20                  25                  30

Leu Asp Val Pro Asp Ile Ile Ile Thr Pro Pro Thr Pro Thr Gly Met
        35                  40                  45

Met Leu Pro Arg Asp Ser Gly Ser Thr Val Trp Leu Asp Glu Thr Gly
    50                  55                  60

Ser Cys Pro Asp Asp Gly Glu Ile Asp Pro Glu Ala
65                  70                  75

<210> SEQ ID NO 5
<211> LENGTH: 76
<212> TYPE: PRT
<213> ORGANISM: Canis lupus

<400> SEQUENCE: 5

Met Gly Leu Lys Leu Ser Cys Leu Lys Gly Leu Lys Met Cys Gly Ser
1               5                   10                  15

Ser Ser Gly Ser Ser His Asp Glu Ala Pro Val Leu Ser Asp Lys His
            20                  25                  30

Leu Asp Val Pro Asn Ile Ile Ile Thr Pro Pro Thr Pro Thr Gly Met
        35                  40                  45
```

-continued

```
Met Leu Pro Arg Asp Ser Arg Gln Thr Val Trp Leu Asp Glu Thr Gly
    50                  55                  60

Ser Cys Pro Glu Asp Gly Glu Ile Asp Pro Glu Ala
65                  70                  75

<210> SEQ ID NO 6
<211> LENGTH: 75
<212> TYPE: PRT
<213> ORGANISM: Bos taurus

<400> SEQUENCE: 6

Met Gly Leu Lys Leu Thr Cys Leu Lys Gly Leu Lys Met Cys Val Ser
1               5                   10                  15

Ser Ser Gly Ser His Asp Glu Ala Pro Val Leu Ser Asp Lys His Leu
                20                  25                  30

Asp Val Pro Asn Ile Ile Ile Thr Pro Pro Thr Pro Thr Gly Val Ala
            35                  40                  45

Leu Pro Arg Asp Thr Arg Arg Ala Val Trp Leu Asp Glu Ser Gly Ser
        50                  55                  60

Cys Thr Glu Asp Gly Asp Leu Asp Pro Glu Ala
65                  70                  75

<210> SEQ ID NO 7
<211> LENGTH: 111
<212> TYPE: PRT
<213> ORGANISM: Rattus norvegicus

<400> SEQUENCE: 7

Met Thr Pro Ala Ala His Gly Cys Arg Arg Val Ala Trp Cys Pro Ser
1               5                   10                  15

Arg Gln Pro Ala Ser Ala Pro Ser Ala Pro Gln Glu Ala Ala Arg Arg
                20                  25                  30

Gly Asp Ala Met Gly Leu Lys Pro Ser Cys Leu Lys Gly Phe Lys Met
            35                  40                  45

Cys Val Ser Ser Ser Ser Asn Asn His Asp Glu Ala Pro Val Leu Asn
        50                  55                  60

Asp Lys His Leu Ser Val Pro Asn Ile Ile Ile Thr Pro Pro Thr Pro
65                  70                  75                  80

Thr Gly Met Gly Leu Ser Arg Asp Ser Asn Ser Gln Val Trp Met Asp
                85                  90                  95

Glu Leu Gly Ser Tyr Gln Asp Asp Glu Glu Leu Glu Pro Glu Val
            100                 105                 110

<210> SEQ ID NO 8
<211> LENGTH: 899
<212> TYPE: DNA
<213> ORGANISM: Homo sapiens

<400> SEQUENCE: 8
cccgagcgcc ggccgggcca tgaccccgc tgctctgtct tgcaggctcg tcgccgcggc        60 ccccgagcc cgaccgccgc cgccaccacc accagcgccc gggcgggcct cgcgcgcctc       120
gggcgcggct ccgcagtgag cccaccaaga aggaagcggc ctgcagaggt gccgacatgg       180
ggcttaagat gtcctgcctg aaaggctttc aaatgtgtgt cagcagcagc agcagcagcc       240
acgacgaggc ccccgtcctg aacgacaagc acctggacgt gcccgacatc atcatcacgc       300
cccccacccc cacgggcatg atgctgccga gggacttggg gagcacagtc tggctggatg       360
```

-continued

```
agacagggtc gtgcccagat gatggagaaa tcgacccaga agcctgagga ggtgtcctgg    420
gtttggctgg ctggctcctg ctccagcggc ccggcttcag gtgtccgggg gcgtggctgc    480
ctggagcagg tgtgctgaat accctggatg ggaactgagc gaacccgggc ctccgctcag    540
agagacgtgg caggaccagc gaggaatcca gcctgtccac ttccagaaca gtgtttccca    600
ggccccgctg agtggaccgg acctctgaca cctccaggtt cttgctgact ccggcctggt    660
gaaagggagc gccatggtcc tggctgttgg ggtcccaggg agaggctctc ttctggacaa    720
acacaccctc ccagccccca gggctgtgca aacacatgcc cctgccataa gcaccaacaa    780
gaacttcttg caggtggagt ggctgttttt tataagttgt tttacagata cggaaacagt    840
ccaaaatggg atttataatt tcttttttgc attataaata aagatcctct gtaacaaaa     899
```